United States Patent
Ding et al.

(10) Patent No.: US 9,177,222 B2
(45) Date of Patent: Nov. 3, 2015

(54) EDGE MEASUREMENT VIDEO TOOL AND INTERFACE INCLUDING AUTOMATIC PARAMETER SET ALTERNATIVES

(71) Applicant: Mitutoyo Corporation, Kawasaki (JP)

(72) Inventors: Yuhua Ding, Bellevue, WA (US); Robert Kamil Bryll, Bothell, WA (US); Mark Lawrence Delaney, Shoreline, WA (US); Michael Nahum, Kirkland, WA (US)

(73) Assignee: Mitutoyo Corporation, Kanagawa-ken (JP)

( * ) Notice: Subject to any disclaimer, the term of this patent is extended or adjusted under 35 U.S.C. 154(b) by 441 days.

(21) Appl. No.: 13/718,986

(22) Filed: Dec. 18, 2012

(65) Prior Publication Data

US 2014/0126804 A1    May 8, 2014

Related U.S. Application Data

(63) Continuation-in-part of application No. 13/669,333, filed on Nov. 5, 2012, now Pat. No. 8,689,127.

(51) Int. Cl.
*G06K 9/46* (2006.01)
*G01N 21/88* (2006.01)
*G06T 7/00* (2006.01)

(52) U.S. Cl.
CPC .......... *G06K 9/4604* (2013.01); *G01N 21/8806* (2013.01); *G06T 7/0085* (2013.01); *G06T 2200/24* (2013.01); *G06T 2207/20092* (2013.01); *G06T 2207/30108* (2013.01)

(58) Field of Classification Search
None
See application file for complete search history.

(56) References Cited

U.S. PATENT DOCUMENTS

| | | | |
|---|---|---|---|
| 6,542,180 B1 | 4/2003 | Wasserman et al. | |
| 6,748,110 B1 | 6/2004 | Wallack | |
| 7,324,682 B2 | 1/2008 | Wasserman | |
| 7,454,053 B2 | 11/2008 | Bryll et al. | |
| 7,567,713 B2 | 7/2009 | Ding | |
| 7,636,449 B2 * | 12/2009 | Mirtich et al. | 382/100 |
| 8,111,905 B2 | 2/2012 | Campbell | |

(Continued)

OTHER PUBLICATIONS

Mitutoyo Corporation & Micro Encoder Inc., "QVPAK 3D CNC Vision Measuring Machine Operation Guide," Version 2.0, published Sep. 1996, 86 pages.

(Continued)

*Primary Examiner* — Matt Kim
*Assistant Examiner* — Maryam Ipakchi
(74) *Attorney, Agent, or Firm* — Seed IP Law Group PLLC

(57) ABSTRACT

A user interface for setting parameters for an edge location video tool is provided. In one implementation, the user interface includes a multi-dimensional parameter space representation with edge zones that allows a user to adjust a single parameter combination indicator in a zone in order to adjust multiple edge detection parameters for detecting a corresponding edge. The edge zones indicate the edge features that are detectable when the parameter combination indicator is placed within the edge zones. In another implementation, representations of multiple edge features that are detectable by different possible combinations of the edge detection parameters are automatically provided in one or more windows. When a user selects one of the edge feature representation, the corresponding combination of edge detection parameters is set as the parameters for the edge location video tool.

20 Claims, 12 Drawing Sheets

(56) References Cited

U.S. PATENT DOCUMENTS

| | | |
|---|---|---|
| 8,111,938 B2 | 2/2012 | Bryll et al. |
| 8,127,247 B2 | 2/2012 | Tremblay et al. |
| 8,271,895 B2 | 9/2012 | Tseo et al. |
| 8,280,172 B1 | 10/2012 | Campbell et al. |
| 8,295,552 B2 * | 10/2012 | Mirtich et al. ............... 382/107 |
| 2003/0067496 A1 | 4/2003 | Tasker et al. |
| 2004/0120571 A1 * | 6/2004 | Duvdevani et al. ........... 382/149 |
| 2005/0109959 A1 * | 5/2005 | Wasserman et al. ..... 250/559.19 |
| 2005/0275831 A1 * | 12/2005 | Silver ......................... 356/237.1 |
| 2005/0276445 A1 | 12/2005 | Silver et al. |
| 2006/0011725 A1 * | 1/2006 | Schnee ......................... 235/454 |
| 2006/0093205 A1 * | 5/2006 | Bryll et al. ................... 382/152 |
| 2007/0014467 A1 * | 1/2007 | Bryll ............................ 382/152 |
| 2007/0146491 A1 | 6/2007 | Tremblay et al. |
| 2007/0183666 A1 | 8/2007 | Ding |
| 2009/0088999 A1 | 4/2009 | Bryll et al. |
| 2009/0273668 A1 * | 11/2009 | Mirtich et al. ................ 348/86 |
| 2010/0138028 A1 | 6/2010 | Tasker et al. |
| 2010/0158343 A1 * | 6/2010 | Bryll ............................ 382/141 |
| 2011/0231787 A1 * | 9/2011 | Tseo et al. ................... 715/771 |
| 2012/0150029 A1 | 6/2012 | Debuc |

OTHER PUBLICATIONS

Mitutoyo Corporation & Micro Encoder Inc., "QVPAK 3D CNC Vision Measuring Machine User's Guide," Version 7, published Jan. 2003, 330 pages.

Mitutoyo Corporation & Micro Encoder Inc., "QVPAK CNC Vision Measuring Machine Software User's Guide," published Oct. 2011, 346 pages.

Adobe Systems Incorporated, "Color Variations Tool in Adobe Photoshop," screenshot captured May 2012, 1 page.

Gregoire et al., "Hausdorff distance between convex polygons," Fall 1998, <http://cgm.cs.mcgill.ca/~godfried/teaching/cg-projects/98/normand/main.html, downloaded on Dec. 3, 2012, 12 pages.

Nikon Corporation, "Nexiv Software," www.nikon.com/products/instruments/lineup/industrial/nexiv/others/soft/index.htm, internet accessed on Jan. 9, 2013, 12 pages.

U.S. Appl. No. 13/669,333, for "Edge Measurement Video Tool Parameter-Setting Interface," filed Nov. 5, 2012, 33 pages.

* cited by examiner

EDGE MEASUREMENT VIDEO TOOL AND INTERFACE INCLUDING AUTOMATIC PARAMETER SET ALTERNATIVES

CROSS-REFERENCE TO RELATED APPLICATION(S)

This application is a continuation-in-part of U.S. patent application Ser. No. 13/669,333, entitled "EDGE MEASUREMENT VIDEO TOOL PARAMETER-SETTING USER INTERFACE" filed on Nov. 5, 2012, the disclosure of which is hereby incorporated by reference in its entirety.

BACKGROUND

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the QVPAK 3D CNC Vision Measuring Machine User's Guide, published January 2003, and the QVPAK 3D CNC Vision Measuring Machine Operation Guide, published September 1996, each of which is hereby incorporated by reference in their entirety. This product, as exemplified by the QV-302 Pro model, for example, is able to use a microscope-type optical system to provide images of a workpiece at various magnifications, and move the stage as necessary to traverse the workpiece surface beyond the limits of any single video image. A single video image typically encompasses only a portion of the workpiece being observed or inspected, given the desired magnification, measurement resolution, and physical size limitations of such systems.

Machine vision inspection systems generally utilize automated video inspection. U.S. Pat. No. 6,542,180 (the '180 patent) teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode which progressively "learns" the inspection event sequence by storing a sequence of machine control instructions corresponding to a sequence of inspection operations performed by a user with the aid of a graphical user interface, or through a combination of both methods. Such a recording mode is often referred to as "learn mode" or "training mode" or "record mode." Once the inspection event sequence is defined in "learn mode," such a sequence can then be used to automatically acquire (and additionally analyze or inspect) images of a workpiece during "run mode."

The machine control instructions including the specific inspection event sequence (i.e., how to acquire each image and how to analyze/inspect each acquired image) are generally stored as a "part program" or "workpiece program" that is specific to the particular workpiece configuration. For example, a part program defines how to acquire each image, such as how to position the camera relative to the workpiece, at what lighting level, at what magnification level, etc. Further, the part program defines how to analyze/inspect an acquired image, for example, by using one or more video tools such as edge/boundary detection video tools.

Video tools (or "tools" for short) and other graphical user interface features may be used manually to accomplish manual inspection and/or machine control operations (in "manual mode"). Their set-up parameters and operation can also be recorded during learn mode, in order to create automatic inspection programs, or "part programs". Video tools may include, for example, edge/boundary detection tools, autofocus tools, shape or pattern matching tools, dimension measuring tools, and the like.

Various methods are known for locating edge features in workpiece images. For example, various algorithms are known which apply brightness gradient operators to images which include an edge feature to determine its location, e.g. a Canny Edge detector or a differential edge detector. Such edge detection algorithms may be included in the machine vision inspection systems which also use carefully configured illumination and/or special image processing techniques to enhance brightness gradients or otherwise improve edge location accuracy and repeatability.

Some machine vision systems (e.g. those utilizing the QVPAK® software described above) provide edge location video tools which have adjustable parameters for an edge detection algorithm. In certain implementations, the parameters may initially be determined for an edge on a representative workpiece during a learn mode operation and then utilized during a run mode operation to find the corresponding edge of a similar workpiece. When desirable edge detection parameters are difficult or impossible to determine automatically during the learn mode, the user may choose to adjust the parameters manually. However certain edge detection parameters (e.g. thresholds such as TH, THR, and THS, outlined herein) are considered to be difficult to understand for the majority of users (e.g. relatively unskilled users), and how their adjustment affects a particular edge detection operation is considered difficult to visualize, particularly for a combination of parameters. The adjustments of the parameters may be further complicated by the variety of edge conditions and workpiece materials in part to part variations encountered when programming and using general purpose machine vision inspection system. An improved method and system that allows relatively unskilled users to adjust the parameters of edge location video tools so that they can be used to reliably inspect a variety of types of edges would be desirable.

BRIEF DESCRIPTION OF THE DRAWINGS

FIG. 9 is a diagram illustrating various features of a third embodiment of a user interface display including different edge feature representations that a user can select from.

FIG. 10 is a flow diagram of a method utilizing an exhaustive search for determining and displaying different edge feature representations that a user can select from.

FIG. 11 is a flow diagram of a method utilizing connected edges for determining and displaying different edge feature representations that a user can select from.

DETAILED DESCRIPTION

Figure 1:
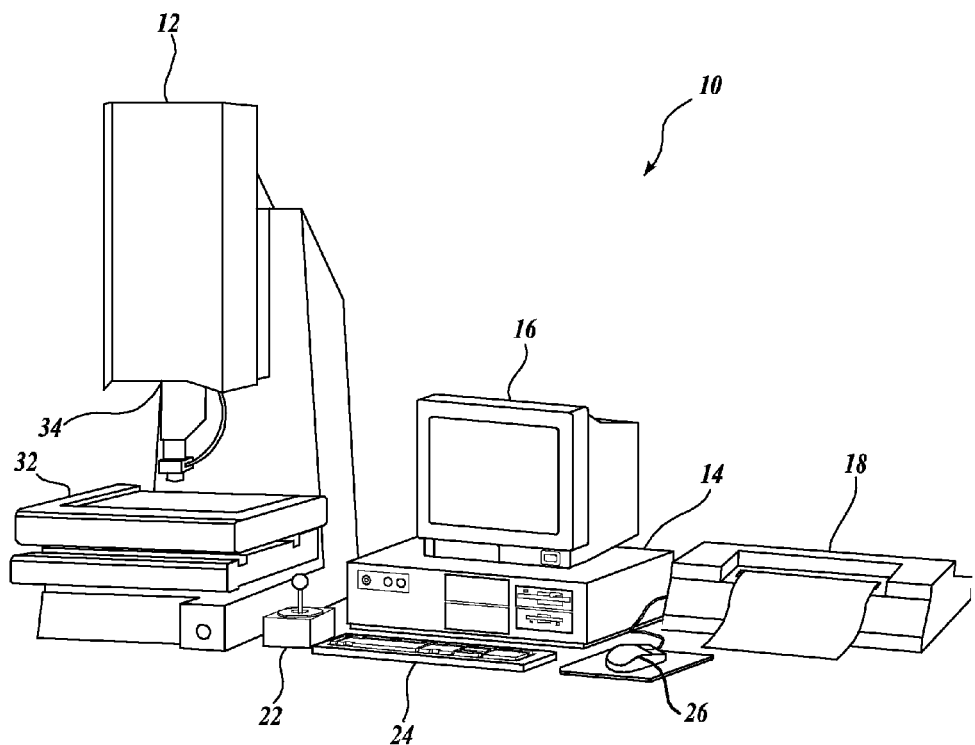
FIG. 1 is a diagram showing various typical components of a general purpose precision machine vision inspection system.

A method for defining edge detection parameters in a machine vision inspection system user interface is provided. In one embodiment, the method begins by providing an edge location video tool having a plurality of edge detection parameters. A region of interest (ROI) is defined for the edge location video tool, including at least a first respective edge feature in the region of interest. A plurality of candidate parameter combinations of the plurality of edge detection parameters are automatically determined, wherein respective candidate parameter combinations are usable to detect respective edge features in the region of interest. The user interface is operated to display respective candidate parameter combination representations corresponding to the respective candidate parameter combinations usable to detect respective edge features in the region of interest. The user interface is configured to allow a user to perform a parameter combination selection action relative to the displayed respective candidate parameter combination representations. The user selection action results in a selection of a combination of edge detection parameters that govern operation of the edge location video tool in the defined region of interest.

The user interface may comprise a multi-dimensional parameter space representation of possible combinations of the plurality of edge detection parameters. The step of determining a plurality of candidate parameter combinations may comprise determining a first set of respective candidate parameter combinations usable to detect the first respective edge feature. The step of operating the user interface may comprise displaying a representation of a first set of respective candidate parameter combinations as a first zone in the multi-dimensional parameter space representation. The user interface may be configured to allow a user to perform a parameter combination selection action relative to the first zone, comprising moving a parameter combination indicator to a location within the first zone and operating the parameter combination indicator to select the parameter combination corresponding to that location.

The region of interest (ROI) may include at least a second respective edge feature in the region of interest. The step of determining a plurality of candidate parameter combinations may comprise determining a second set of respective candidate parameter combinations usable to detect the second respective edge feature. The step of operating the user interface may comprise displaying a representation of the second set of respective candidate parameter combinations as a second zone in the multi-dimensional parameter space representation.

The user interface may comprise at least one edge feature representation window that includes an image of the field of view of the machine vision inspection system and a representation of the edge features detectable by the combination of parameters indicated by a current configuration of the parameter combination indicator superimposed on the image of the field of view. The representation of the edge features detectable by the combination of parameters indicated by the current configuration of the parameter combination indicator may comprise a plurality of detectable edge points, corresponding to a plurality of scan lines across the ROI, superimposed on the image of the field of view. The at least one edge feature representation window and the multi-dimensional parameter space representation may be synchronized such that an adjustment or selection in the at least one edge feature representation window results in a corresponding indication in the multi-dimensional parameter space representation.

The region of interest (ROI) may include at least a second respective edge feature in the region of interest. The user interface may comprise a representation of the first and second respective edge features. The step of automatically determining a plurality of candidate parameter combinations may comprise determining at least a first respective candidate parameter combination usable to detect the first respective edge feature, and determining at least a second respective candidate parameter combination usable to detect the second respective edge feature. The step of operating the user interface may comprise displaying the representation of the first and second respective edge features.

The user interface may be configured to allow a user to perform a parameter combination selection action relative to the displayed representations of the first and second respective edge features, comprising moving a cursor to a location proximate to the representation of a desired one of the first and second respective edge features and operating the cursor to select the parameter combination corresponding to that edge. The representation of the first and second respective edge features may comprise a first indicator superimposed on an image of the first respective edge feature indicating that a corresponding first respective candidate parameter combination has been determined, and a second indicator superimposed on an image of the second respective edge feature indicating that a corresponding second respective candidate parameter combination has been determined. The first and second indicators may comprise detected edge points along the first and second edge features, respectively.

The representation of the first respective edge feature may comprise a first edge window including the first respective edge feature indicating that a corresponding first respective candidate parameter combination has been determined, and the representation of the second respective edge feature may comprise a second edge window including the second respective edge feature indicating that a corresponding second respective candidate parameter combination has been determined. The user interface may be configured to allow a user to perform a parameter combination selection action relative to the displayed representations of the first and second respective edge features, comprising moving a cursor to a location in a desired one of the first and second edge windows and operating the cursor to select the parameter combination corresponding to that edge.

The user interface may further comprise a multi-dimensional parameter space representation of possible combinations of the plurality of edge detection parameters. The user interface may be configured to allow a user to perform a parameter combination selection action relative to the displayed representations of the first and second respective edge features. The selection action may comprise moving a cursor to a location proximate to the representation of a desired one of the first and second respective edge features and operating the cursor to select either the first or second respective edge feature. In response to the selection, the user interface may be further configured to display a representation of a first or second zone. More specifically, a representation of a first set of respective candidate parameter combinations may be displayed as a first zone in the multi-dimensional parameter space representation if the first respective edge feature is selected, wherein the first set of respective parameter combinations comprises the first respective candidate parameter combination usable to detect the first respective edge feature in addition to other candidate parameter combinations usable to detect the first respective edge feature. Alternatively, a representation of a second set of respective candidate parameter combinations may be displayed as a second zone in the multi-dimensional parameter space representation if the second respective edge feature is selected, wherein the second set of respective parameter combinations comprises the second respective candidate parameter combination usable to detect the second respective edge feature in addition to other candidate parameter combinations usable to detect the second respective edge feature.

In one embodiment, a method for defining edge location parameters in a machine vision inspection system user interface is provided. A plurality of edge detection parameters for a region of interest (ROI) of an edge location video tool is defined. A multi-dimensional parameter space representation is displayed which indicates possible combinations of the plurality of edge detection parameters. In one implementation, the multi-dimensional parameter space representation is a two dimensional grid, with each dimension indicating possible values corresponding to one of the edge detection parameters. A parameter combination indicator (e.g. including a parameter combination marker that can be selected and dragged in a user interface) is located within the multidimensional parameter space representation which indicates a combination of the edge detection parameters based on its location. One or more edge feature representation windows are displayed which represent edge features located in the ROI of the edge location video tool. In one embodiment, edge features detectable by the combination of edge detection parameters indicated by a current configuration of the parameter combination indicator are automatically updated in the one or more edge feature representation windows. It should be appreciated that the term window used herein includes previously known types of user interface windows, and also refers more generally to unconventional elements of a user interface that may include one or more user interface characteristics such as: they may include display elements made more compact than an entire display area and/or may be hidden at some times (e.g. as resized and/or relocated and/or hidden by a user), they may focus on a particular class of information and/or menus or selections related to a particular class of information, and so on. Thus, particular forms of windows illustrated herein are exemplary only and not limiting. For example, in some embodiments, a "window" may not have a well-defined limiting boundary or the like, it may have hyper-link like behavior, it may appear on a separate and/or isolated display element, and so on.

The edge feature representation windows may include representations of a scanline intensity and/or scanline intensity gradient of the region of interest of the edge location video tool. Another edge feature representation window may include an image of the field of view of the machine vision inspection system. A representation of one or more of the edge features detectable by the combination of parameters indicated by a current configuration of the parameter combination indicator may be superimposed on the representation of the scanline intensity and/or scanline intensity gradient and/or the image of the field of view.

The edge feature representation windows and the multi-dimensional parameter space representation may be synchronized such that a parameter adjustment or selection in one of the edge feature representation windows results in a corresponding adjustment or selection of the parameter indicator (e.g. its position) in the multi-dimensional parameter space representation. The adjustment or selection in the edge feature representation window may comprise an adjustment or selection of a threshold level, and the corresponding indication in the multi-dimensional parameter space representation may comprise a movement of the parameter combination indicator to a location which corresponds to the selected threshold level.

Various embodiments of the invention are described below. The following description provides specific details for a thorough understanding and an enabling description of these embodiments. One skilled in the art will understand, however, that the invention may be practiced without many of these details. In addition, some well-known structures or functions may not be shown or described in detail, so as to avoid unnecessarily obscuring the relevant description of the various embodiments. The terminology used in the description presented below is intended to be interpreted in its broadest reasonable manner, even though it is being used in conjunction with a detailed description of certain specific embodiments of the invention.

FIG. 1 is a block diagram of one exemplary machine vision inspection system 10 usable in accordance with methods described herein. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10. It will be appreciated that in various embodiments, a touchscreen tablet or the like may be substituted for and/or redundantly provide the functions of any or all of the computer system 14, the display 16, the joystick 22, a keyboard 24, and the mouse 26.

Those skilled in the art will appreciate that the controlling computer system 14 may generally consist of any computing system or device. Suitable computing systems or devices may include personal computers, server computers, minicomputers, mainframe computers, distributed computing environments that include any of the foregoing, and the like. Such computing systems or devices may include one or more processors that execute software to perform the functions described herein. Processors include programmable general-purpose or special-purpose microprocessors, programmable controllers, application specific integrated circuits (ASICs), programmable logic devices (PLDs), or the like, or a combination of such devices. Software may be stored in memory, such as random access memory (RAM), read-only memory (ROM), flash memory, or the like, or a combination of such components. Software may also be stored in one or more storage devices, such as magnetic or optical based disks, flash memory devices, or any other type of non-volatile storage medium for storing data. Software may include one or more program modules which include routines, programs, objects, components, data structures, and so on that perform particular tasks or implement particular abstract data types. In distributed computing environments, the functionality of the program modules may be combined or distributed across multiple computing systems or devices and accessed via service calls, either in a wired or wireless configuration.

The vision measuring machine 12 includes a moveable workpiece stage 32 and an optical imaging system 34 which may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. The machine vision inspection system 10 is also described in commonly assigned U.S. Pat. Nos. 7,454,053, 7,324,682, 8,111,905, and 8,111,938, which are each incorporated herein by reference in their entireties.

Figure 2:
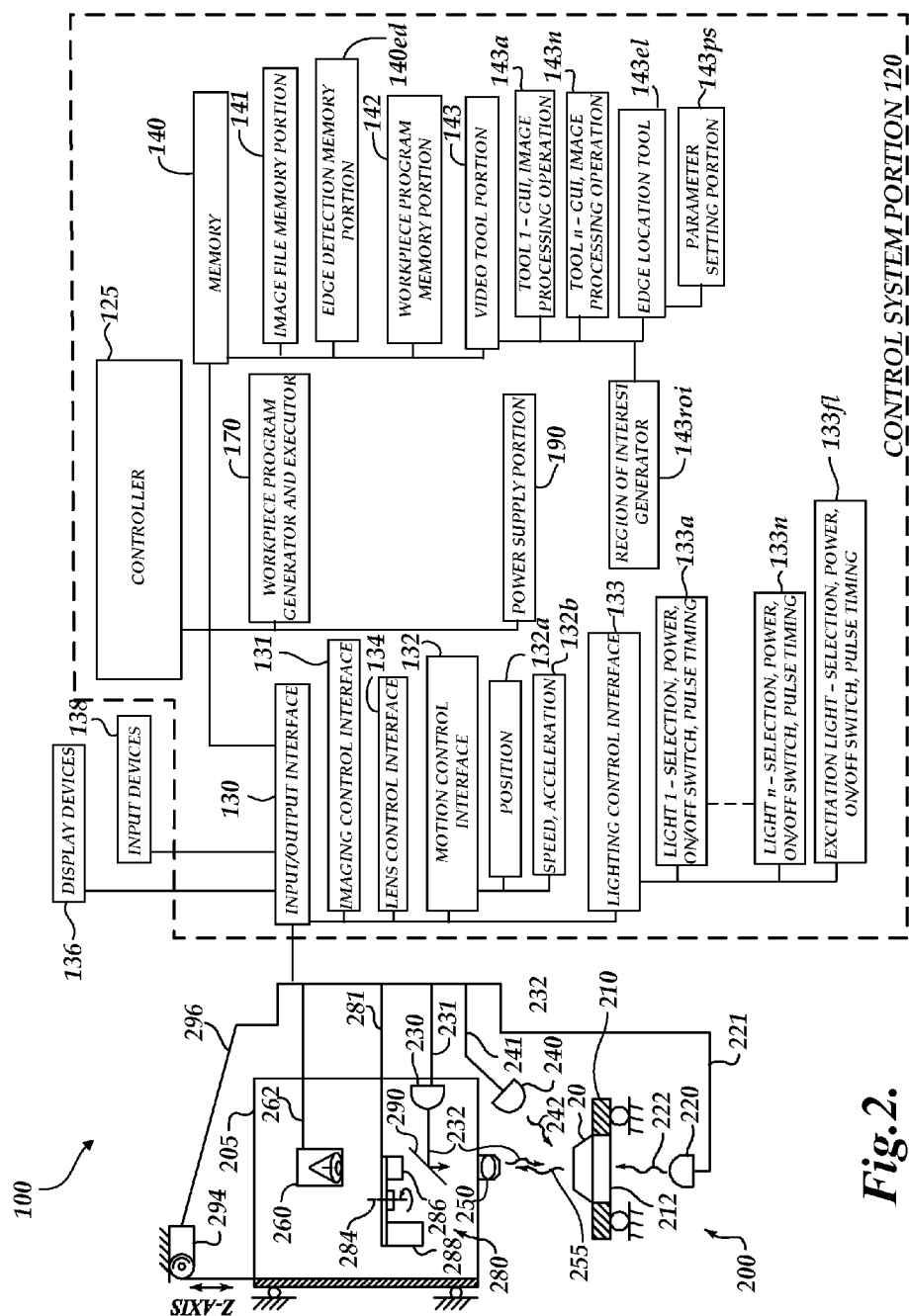
FIG. 2 is a block diagram of a control system portion and a vision components portion of a machine vision inspection system similar to that of FIG. 1, and including features as described herein.

FIG. 2 is a block diagram of a control system portion 120 and a vision components portion 200 of a machine vision inspection system 100 similar to the machine vision inspection system of FIG. 1, and including features as described herein. As will be described in more detail below, the control system portion 120 is utilized to control the vision components portion 200. The vision components portion 200 includes an optical assembly portion 205, light sources 220, 230, and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280 having lenses 286 and 288. Alternatively to the turret lens assembly, a fixed or manually interchangeable magnification-altering lens, or a zoom lens configuration, or the like, may be included.

The optical assembly portion 205 is controllably movable along a Z-axis that is generally orthogonal to the X and Y axes, by using a controllable motor 294 that drives an actuator to move the optical assembly portion 205 along the Z-axis to change the focus of the image of the workpiece 20. The controllable motor 294 is connected to the input/output interface 130 via a signal line 296.

A workpiece 20, or a tray or fixture holding a plurality of workpieces 20, which is to be imaged using the machine vision inspection system 100 is placed on the workpiece stage 210. The workpiece stage 210 may be controlled to move relative to the optical assembly portion 205, such that the interchangeable objective lens 250 moves between locations on a workpiece 20, and/or among a plurality of workpieces 20. One or more of a stage light 220, a coaxial light 230, and a surface light 240 (e.g. a ring light) may emit source light 222, 232, and/or 242, respectively, to illuminate the workpiece or workpieces 20. The light source 230 may emit light 232 along a path including a mirror 290. The source light is reflected or transmitted as workpiece light 255, and the workpiece light used for imaging passes through the interchangeable objective lens 250 and the turret lens assembly 280 and is gathered by the camera system 260. The image of the workpiece(s) 20, captured by the camera system 260, is output on a signal line 262 to the control system portion 120. The light sources 220, 230, and 240 may be connected to the control system portion 120 through signal lines or busses 221, 231, and 241, respectively. To alter the image magnification, the control system portion 120 may rotate the turret lens assembly 280 along axis 284 to select a turret lens, through a signal line or bus 281.

As shown in FIG. 2, in various exemplary embodiments, the control system portion 120 includes a controller 125, the input/output interface 130, a memory 140, a workpiece program generator and executor 170, and a power supply portion 190. Each of these components, as well as the additional components described below, may be interconnected by one or more data/control buses and/or application programming interfaces, or by direct connections between the various elements.

The input/output interface 130 includes an imaging control interface 131, a motion control interface 132, a lighting control interface 133, and a lens control interface 134. The motion control interface 132 may include a position control element 132a, and a speed/acceleration control element 132b although such elements may be merged and/or indistinguishable. The lighting control interface 133 includes lighting control elements 133a-133n, and 133fl which control, for example, the selection, power, on/off switch, and strobe pulse timing if applicable, for the various corresponding light sources of the machine vision inspection system 100.

The memory 140 may include an image file memory portion 141, an edge detection memory portion 140ed, a workpiece program memory portion 142 that may include one or more part programs, or the like, and a video tool portion 143. The video tool portion 143 includes video tool portion 143a and other video tool portions (e.g. 143n), which determine the GUI, image processing operation, etc., for each of the corresponding video tools, and a region of interest (ROI) generator 143roi that supports automatic, semi-automatic and/or manual operations that define various ROIs that are operable in various video tools included in the video tool portion 143.

In the context of this disclosure, and as known by one of ordinary skill in the art, the term video tool generally refers to a relatively complex set of automatic or programmed operations that a machine vision user can implement through a relatively simple user interface (e.g. a graphical user interface, editable parameter windows, menus, and the like), without creating the step-by-step sequence of operations included in the video tool or resorting to a generalized text-based programming language, or the like. For example, a video tool may include a complex pre-programmed set of image processing operations and computations which are applied and customized in a particular instance by adjusting a few variables or parameters that govern the operations and computations. In addition to the underlying operations and computations, the video tool comprises the user interface that allows the user to adjust those parameters for a particular instance of the video tool. For example, many machine vision video tools allow a user to configure a graphical region of interest (ROI) indicator through simple "handle dragging" operations using a mouse, in order to define the location parameters of a subset of an image that is to be analyzed by the image procession operations of a particular instance of a video tool. It should be noted that the visible user interface features are sometimes referred to as the video tool, with the underlying operations being included implicitly.

In common with many video tools, the edge location and parameter setting subject matter of this disclosure includes both user interface features and underlying image processing operations, and the like, and the related features may be characterized as features of an edge location tool 143el and corresponding parameter setting portion 143ps included in the video tool portion 143. The edge location tool 143el may utilize an algorithm for determining edge locations. The algorithm may be governed by edge detection parameters, which may be determined and programmed automatically in some cases during learn mode, and/or manually adjusted by a user (e.g. thresholds such as TH, THR, and THS, described in greater detail below.)

In one implementation, in order that a user may manually set edge detection video tool parameters as outlined above, the parameter setting portion 143ps provides a multi-dimensional parameter space representation (e.g. a 2-dimensional grid with TH on one axis and THS on the other axis). A parameter marker or indicator (e.g. cursor) is provided that can be moved within the parameter space representation by a user to adjust or select a desired parameter combination (e.g. of TH and THS). Parameter combination edge zones are provided within the parameter space representation which indicate locations where the parameter indicator may be positioned to detect certain edge features. One or more edge feature representation windows (e.g. showing a scanline intensity and/or a scanline intensity gradient and/or a field of view of the machine vision system) are provided which illustrate changes to the parameters and/or the edge features that are detectable according to the current configuration, as will be described in more detail below with respect to FIGS. 3, 4, 7 and 8. The system may also or alternatively automatically scan the search space of the edge detection parameters and generate one or more images showing meaningful variations of the edge detection results that occur in response to the changing edge detection parameter values. A user interface display may be provided showing the different meaningful variations that a user can select from (e.g. by clicking on a window or an edge feature), as will be described in more detail below with respect to FIGS. 9-11.

The signal lines or busses 221, 231 and 241 of the stage light 220, the coaxial lights 230 and 230', and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 (e.g., the display 16 of FIG. 1) and one or more input devices 138 (e.g., the joystick 22, keyboard 24, and mouse 26 of FIG. 1) can also be connected to the input/output interface 130. The display devices 136 and input devices 138 can be used to display a user interface, which may include various graphical user interface (GUI) features that are usable to perform inspection operations, and/or to create and/or modify part programs, to view the images captured by the camera system 260, and/or to directly control the vision system components portion 200. The display devices 136 may display user interface features associated with the edge location video tool 143el and parameter setting portion 143ps, described in greater detail below.

In various exemplary embodiments, when a user utilizes the machine vision inspection system 100 to create a part program for the workpiece 20, the user generates part program instructions by operating the machine vision inspection system 100 in a learn mode to provide a desired image acquisition training sequence. For example a training sequence may comprise positioning a particular workpiece feature of a representative workpiece in the field of view (FOV), setting light levels, focusing or autofocusing, acquiring an image, and providing an inspection training sequence applied to the image (e.g. using an instance of one of the video tools on that workpiece feature). The learn mode operates such that the sequence(s) are captured or recorded and converted to corresponding part program instructions. These instructions, when the part program is executed, will cause the machine vision inspection system to reproduce the trained image acquisition and inspection operations to automatically inspect that particular workpiece feature (that is the corresponding feature in the corresponding location) on a run mode workpiece or workpieces which matches the representative workpiece used when creating the part program.

Figure 3:
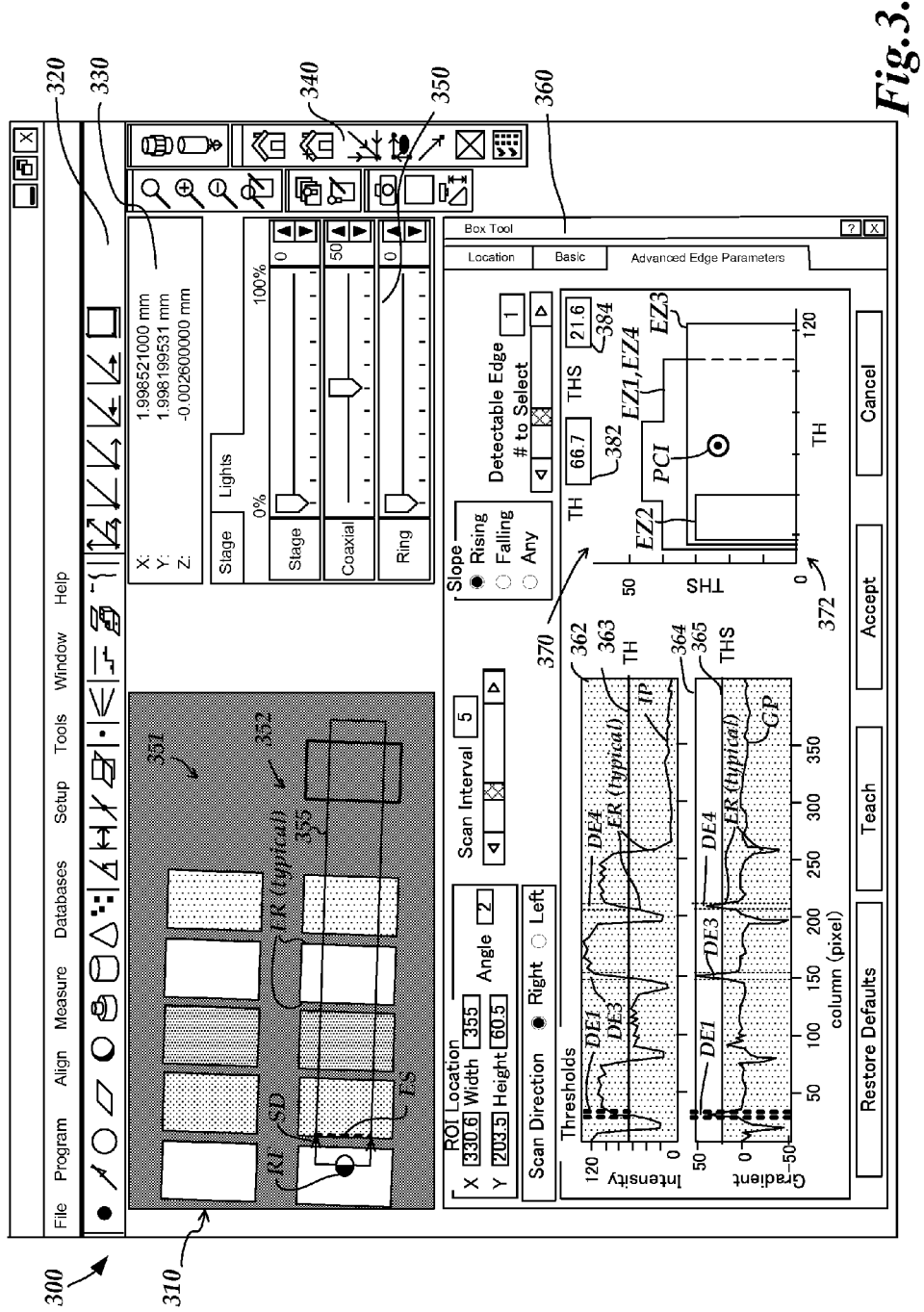
FIGS. 3 and 4 are diagrams illustrating various features of a first embodiment of a user interface display including a multi-dimensional parameter space representation with edge zones and windows including edge feature representations.
Figure 4:
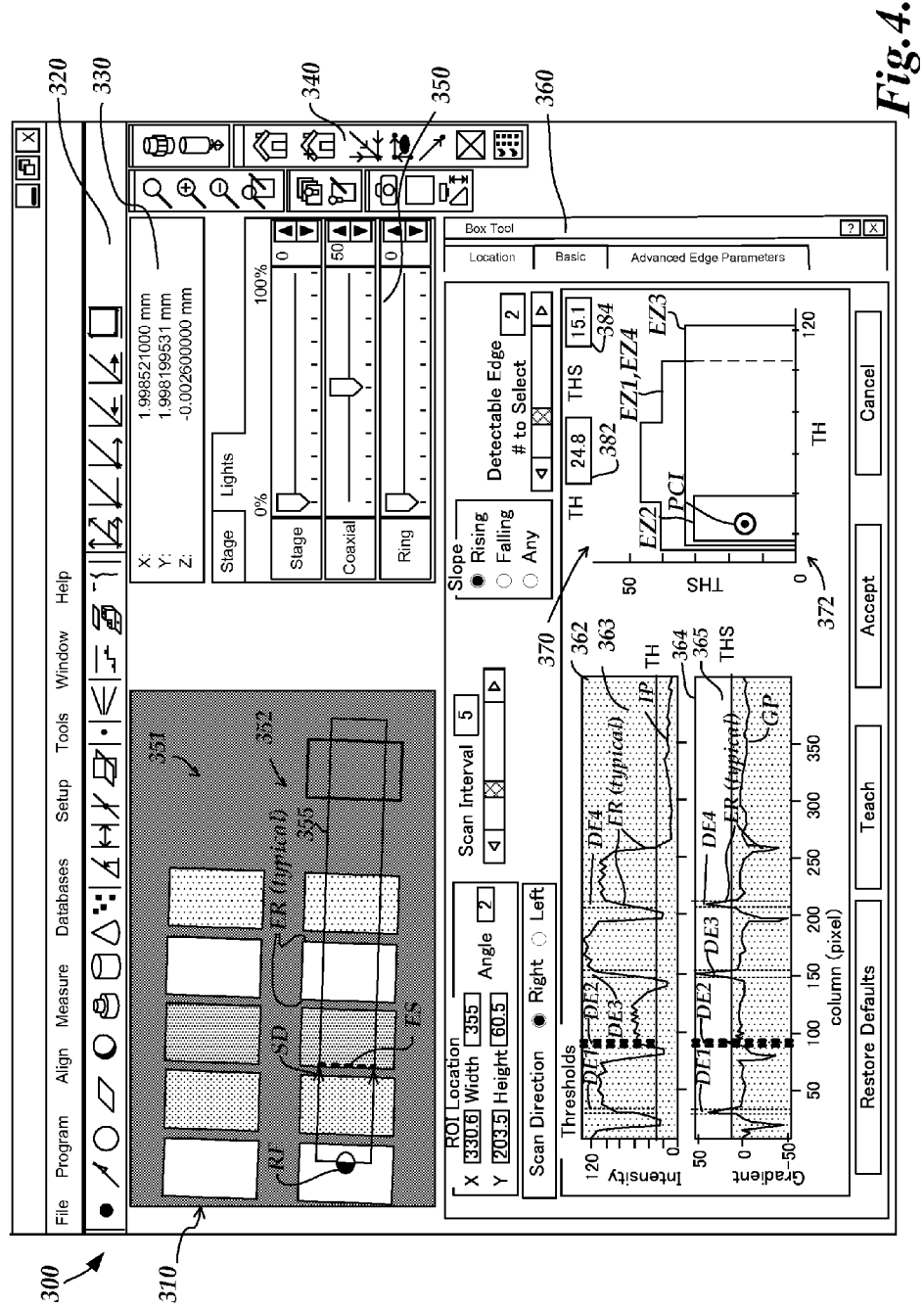

FIGS. 3 and 4 are diagrams illustrating various features of a first embodiment of a user interface display 300 including a field of view window 310 including a workpiece image, various measurement and/or operation selection bars such as the selection bars 320 and 340, a real-time X-Y-Z (position) coordinate window 370, a light control window 350, and an edge detection video tool user interface (a "box tool" user interface) that includes the edge detection parameter window 360, which in the embodiment shown in FIG. 3 is displayed by selecting the "Advanced Edge Parameters" tab of the box tool user interface. The box tool user interface also includes the box tool GUI widget 352 superimposed on the image in the field of view window 310, including a region of interest indicator 355, a rising/falling indicator RF, scan direction arrowheads SD, and an edge selector ES, which are elements known in commercially available systems. The rising/falling indicator RF, in combination with the scan direction arrowheads SD, defines whether detected edges have rising or falling intensity along the scan direction. The edge selector ES indicates the edge that is to be detected (e.g. by the current set of tool parameters.) The edge detection parameter window 360 may also include ROI location parameter/editing box, a scan direction parameter parameter/editing box, a rising/falling edge slope parameter/editing box, a detectable edge number parameter/editing box, and a scan interval parameter/editing box. It will be appreciated that various parameters may have default values and/or values determined automatically based on previous user interface operations or the like.

In the embodiment shown in FIGS. 3 and 4, the edge detection parameter window 360 includes scan line intensity and scan line gradient windows 362 and 364, respectively, as well as a multi-dimensional parameter space representation 370 of possible combinations of a plurality of edge detection parameters (also referred to as edge characteristic parameters), described further below. The scan line intensity window 362 and scan line gradient window 364 illustrate graphs of a scanline intensity profile IP and a scanline intensity gradient profile GP at pixel locations along the scanline direction for a representative scanline (e.g. a central or average scanline, or the like) across the region of interest, and each provides edge feature representations ER of edge features located in the region of interest 355 of the edge location video tool 352. As used herein, an edge feature representation is some form of representation that a user may understand as indicating an edge. In the scan line intensity window 362 edge features are understood to be represented by significant changes in intensity over a relatively limited distance along the scan line. Typical rising edge and a falling edge feature representations ER (one of several cases) are indicated on the scanline intensity profile IP, for example. In the scan line intensity gradient window 364 edge features are understood to be represented by significant gradient changes over a relatively limited distance along the scan line and/or gradient peaks (or valleys). Typical positive and negative gradient edge feature representations ER (one of several cases) are indicated on the scanline intensity gradient profile GP, for example. Of course in the field of view window 310 edge features are understood to be represented by their image, as indicated by the edge feature representations ER, for example. Accordingly, any or all of the windows 310, 362, 364, or the like, may be referred to as an edge representation window. The scanline intensity gradient profile GP may be understood to indicate the slope of the scanline intensity profile IP in this embodiment, thus they will generally have corresponding edge feature representations at corresponding locations along their respective profiles.

In the embodiment shown in FIGS. 3 and 4, the multi-dimensional parameter space representation 370 includes a two dimensional graph 372 showing potential combinations of edge detection parameters TH and THS, with a current combination of the parameters indicated by the location of a parameter combination indicator PCI. The edge features detectable by the current combination of the edge detection parameters TH and THS are displayed and automatically updated in the windows 362 and 364, as described for one exemplary embodiment below.

The edge detection parameters TH and THS are edge detection parameters for an edge detection algorithm of the edge location video tool 352. In one embodiment, these and other settings may be determined during a learn mode of the video tool 352, and then utilized during a run mode for determining edges. When desirable settings are not able to be determined during the learn mode, or when the edge points found by the video tool 352 are determined to not be satisfactory, the user may choose to adjust these settings manually. Some settings for video tools may be intuitive and readily adjustable. However, other settings (e.g., for the edge detection parameters TH and THS) are sometimes considered to be relatively complicated and difficult to adjust, particularly in combination.

The parameters may provide various functions in governing the algorithm. For example, in some cases the parameters may provide a failsafe type function. That is, a parameter that requires a minimum level of brightness change across an edge may prevent an edge detection video tool from returning an edge location in the case of unexpectedly low exposure (e.g. due to a lighting failure), or other anomalous condition. The parameter TH referred to herein defines a threshold that is related to a minimum level of brightness change required across an edge. In another case, a parameter that requires a minimum level of brightness rate of change across an edge (e.g. a gradient value, which may characterize a width or sharpness of an edge) may further characterize a particular instance of an edge, and may prevent an edge detection video tool from returning an edge location in the case of an unexpected change in the form of an edge, or its illumination (e.g. an ambient illumination change, or direction change), or the focus of its image (a blurry image broadens and softens an edge) relative to the "learn mode" edge formation or illumination that was used for the initial training/programming of the video tool. The parameter THS referred to herein defines a threshold that is related to a minimum brightness gradient required across an edge. It will be appreciated that each of the parameters outlined above, and particularly their combination, may be set to correspond to and/or characterize a "prototype" instance of an edge during learn mode, to increase the edge detection reliability and/or specificity (the detection of the expected edge using the expected imaging conditions). The parameters may be set discriminate for a particular edge, or may cause the "failure" of the video tool when the expected conditions are not fulfilled (or nearly fulfilled). In some embodiments, a video tool may be set such that all the parameters are "static", resulting in video tool "failure" unless the expected conditions are strictly reproduced. In some embodiments, a parameter THR (referred to in the incorporated references) may define a relationship between THS and TH, and or a threshold value for that relationship such that video tool may set to adjust some of the parameters (e.g. THS) "dynamically" based on the actual brightness of an image (provided that the brightness falls in a range deemed to provide a reasonable image for inspection), resulting in a video tool that "fails" less often due to expected lighting variations and/or part finish variations, or the like.

In some cases, a number of edges may be crowded together on a workpiece, such that a target edge cannot be reliably isolated by the location and size of a video tool region of interest. In such cases, the parameters outlined above, and particularly their combination, may be set at levels that are satisfied by a target edge (including expected workpiece to workpiece variations), and not satisfied by other nearby edges on the workpiece, such that the video tool discriminates the target edge from the other edges during inspection and measurement operations. It should be appreciated that the inventive features disclosed herein are of particular value for setting a combination of parameters that are useful in this latter case, as well as more generally providing improved ease-of-use and understanding for users.

The intensity window 362 shows an intensity profile IP along a scanline of the edge detection video tool 355 with an adjustable TH line 363. Similarly, the gradient window 364 shows a gradient profile GP along the same scanline of the edge detection video tool 355 with an adjustable THS line 365. The windows 362 and 364 are configured to include operations wherein a user is able to select and adjust the parameter value of the TH line 363 and the THS line 365 graphically (e.g. by dragging the lines) without having to edit the TH and THS text boxes 382 and 384, respectively. This type of display and functionality may be particularly useful for experienced users, for whom the adjustment may be easier and faster than utilizing the prior text box 382 and 384 methods. The location of the parameter combination indicator PCI and the TH and THS text boxes may be updated in real time in response to such a line adjustment. A disadvantage of only utilizing the adjustable lines 363 and 365 is that only one edge detection parameter may be adjusted at a time, and less experienced users may not necessarily know how to interpret the raw intensity profile IP and the gradient profile GP illustrated in the edge feature representation windows 362 and 364.

As illustrated in the windows 362 and 364, in order to increase user understanding of the edge discrimination effect of the TH and THS parameter values, in one embodiment the windows and GUI are configured such that detectable edges DE may be indicated in those windows (that is, the corresponding detectable edge representations along the intensity profile IP and the gradient profile GP may be indicted). In the case shown in FIG. 3, in the gradient window 364, segments of the profile GP that fall below the threshold value for the gradient parameter THS are shaded out. The corresponding segments are shaded out in the intensity window 362, as well. In addition, the portions of the intensity profile that fall below the threshold value for the intensity parameter TH are shaded out in the intensity window 362. Thus, three edge representations that satisfy the current combination of parameters are highlighted or indicated as detectable edges in the windows 362 and 364 by the unshaded areas marked as DE1, DE3 and DE4 in FIG. 3. Such visual indications assist users with understanding how changes in the edge detection parameters TH and THS, separately and in combination, affect the determination of edges and provide a real time indication of how the algorithm is working. In one embodiment (not shown), detectable edge indicators may also be superimposed on the corresponding edges in the field of view window 310, as well. As shown in FIG. 3, because the "detectable edge number to select" box is set to the default value of 1 (meaning the edge to be located is the first detectable edge in the ROI along the scan line direction), the edge selected ES is set for the video tool 352 in the window 310 to the edge corresponding to DE1. The detectable edge DE1 may be marked as the "selected edge" in the window 362 as well, in some embodiments.

In contrast to the individual adjustments of the TH and THS lines 363 and 365 in the windows 362 and 364, the multi-dimensional parameter space representation 370 allows a user to adjust both of the thresholds TH and THS at the same time. In the graph 372, the edge detection parameter TH is represented along the x-axis, while the edge detection parameter THS is represented along the y-axis. The indicator PCI may be selected and dragged by the user to any location on the graph 372, and the current location will define the current TH and THS values. Experiments have shown that by using various features of this user interface even relatively unskilled users can rapidly explore and optimize parameter combinations that reliably isolate particular edges using the various features outlined above, or just as importantly help them understand that an edge cannot be reliably isolated without special conditions (e.g. by selecting a particular detectable edge in the region of interest.)

As an illustrative example for the operation of the user interface in FIGS. 3 and 4, as shown in FIG. 4, the indicator PCI in the graph 372 has been moved to a new location (e.g. by dragging in the user interface). In the embodiment of FIGS. 3 and 4, the windows 362 and 364 are synchronized with the multi-dimensional parameter space representation 370, such that an adjustment in the position of the indicator PCI results in a corresponding adjustment in the level of the TH line 363 and the THS line 365, and vice-versa. Thus, in accordance with the new location of the indicator PCI, the TH line 363 in the window 362 and the THS line 365 in the window 364 have also been correspondingly adjusted. In any case, as a result of the particular new levels defined for the parameters TH and THS, an additional edge, indicated by the reference number DE2 in the windows 362 and 364, is now indicated as a detectable edge. It will be understood by inspection of the figures that the detectable edge DE2 is a "weaker" edge than the edges DE1, DE3 and DE4, and cannot be isolated in the region of interest based solely on the parameters TH and THS. However, it is readily observable that it is the second detectable rising edge along the scan line, and so the user has set the "detectable edge number to select" box to a value of 2. Accordingly, the parameters TH and THS isolate the relatively strong detectable edges DE1-DE4 while rejecting weaker edges and/or noise, and the detectable edge number selector further refines the desired edge to be located—the second detectable edge along the scan line (DE2) using the current set of parameters. In one embodiment, at least one of the windows 362 and 364 (and/or the window 310) and the detectable edge number (e.g. as shown in the detectable edge number to select" box) are synchronized such that a user may select an indicated detectable edge in one of the windows and a corresponding parameter selection is automatically made for the number of the detectable edge along the scan line in the region of interest.

It will be appreciated that one advantage of the multi-dimensional parameter space representation 370 is that it allows the user to adjust multiple parameters (e.g., edge detection parameters TH and THS) at the same time, to rapidly explore the detection margins and other detection reliability tradeoffs (e.g. detection of an incorrect edge vs. the likelihood of tool failure) associated with various combinations of settings. The user need not understand the functions of the various parameters, because by adjusting the location of indicator PCI and observing the real time feedback of a corresponding detectable edge indication, the user intuitively feels the sensitivity of the edge detection results to the location indicator PCI and can intuitively set it in the "best spot" to produce the desired edge detection. Just as importantly, the user may rapidly scan all combinations of parameters by simply sweeping the indicator PCI and learn that no particular combination isolates a target edge, and determine that additional parameters (e.g. the detectable edge number to select" box) may need to be set, or the lighting may need to be changed, or the region of interest adjusted, or the like. In contrast, it is impractical or impossible to make this same determination with the same efficiency and certainty using prior art methods and interfaces for setting edge detection parameters.

While the techniques described above with respect to the multi-dimensional parameter space representation 370 allow a user to adjust multiple edge detection parameters at the same time, it may still be difficult to precisely predict where the indicator PCI will need to be located for the detection of certain edges. As will be described in more detail below, candidate parameter combination edge zones may be provided to assist with the determination of desirable positions for the indicator PCI.

As shown in FIGS. 3 and 4, within the multi-dimensional parameter space representation 370 a candidate parameter combination edge zone EZ1 represents a region in which the indicator PCI can be placed for detecting the first detectable edge DE1. Similarly, a candidate parameter combination edge zone EZ2 represents an area in which the indicator PCI can be placed for detecting the second detectable edge DE2, and a candidate parameter combination edge zone EZ3 represents an area in which the indicator PCI can be placed for detecting the third detectable edge DE3. A fourth candidate parameter combination edge zone EZ4 for detecting the fourth detectable edge DE4 may be considered to completely overlap with the first candidate parameter combination zone EZ1. It will be appreciated that the candidate parameter combination edge zones EZ1, EZ2, EZ3 and EZ4 may all include overlapping areas, in which multiple edges may be detected, and may in some implementations be illustrated with colors or other visible features.

As shown in FIG. 3, to illustrate the use and operation of this feature, the indicator PCI has been placed in a location that is within the candidate parameter combination edge zones EZ1, EZ3, and EZ4, but not within the candidate parameter combination edge zone EZ2. As a result, as illustrated in the windows 362 and 364 and as described above, only the edges DE1, DE3 and DE4 are potentially detectable by the indicated candidate parameter combination. As shown in FIG. 4, the indicator PCI has been moved to a new location where it is within the candidate parameter combination edge zone EZ2, as well as being within the candidate parameter combination edge zones EZ1, EZ3, and EZ4. As a result, each of the edges DE1, DE2, DE3 and DE4 are potentially detectable by the indicated parameter combination, as are indicated in the windows 362 and 364 and as described above.

It will be appreciated that the display of the candidate parameter combination edge zones EZ1, EZ2, EZ3 and EZ4 in this manner allows a user to know where to position the indicator PCI so as to be able to discriminate a desired edge from other edges (if possible), and also what possibilities exist within the multi-dimensional parameter space representation 370 for detecting edges. In one embodiment, the candidate parameter combination edge zones EZ1, EZ2, EZ3 and EZ4 are synchronized with one or more of the windows 310, 362 and 364, wherein a user may select an edge feature to highlight or display a corresponding edge zone EZ. For example, in one of the windows 310, 362 or 364, a user may select (e.g. click on) a detectable edge feature DE or an edge representation ER, in response to which the corresponding candidate parameter combination edge zone EZ is highlighted and/or displayed individually without the other edge zones EZ.

Figure 5:
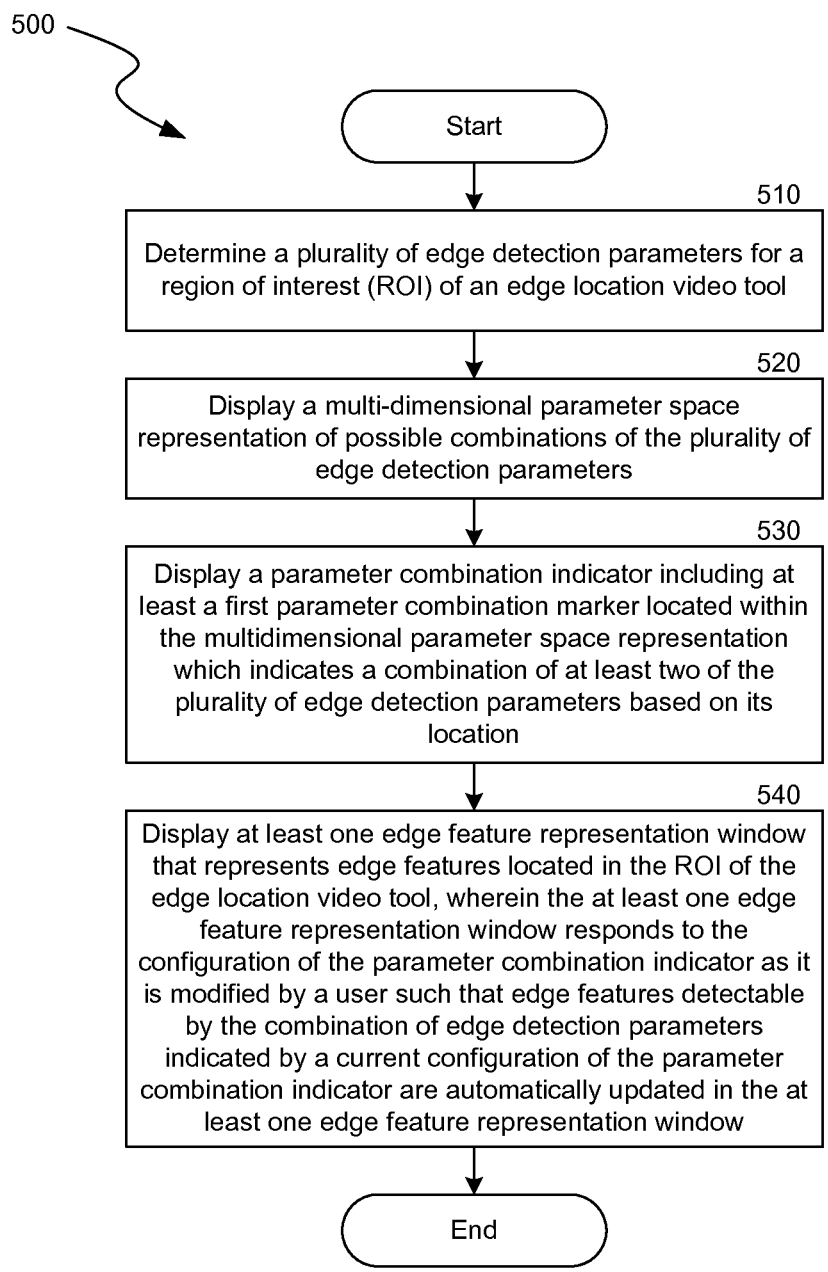
FIG. 5 is a flow diagram of a method for displaying a multi-dimensional parameter space representation and at least one window that includes an edge feature representation.

FIG. 5 is a flow diagram for a method 500 for defining edge detection parameters in a machine vision inspection system user interface. At a block 510, a plurality of edge detection parameters are determined for a region of interest (ROI) of an edge location video tool. At a block 520, a multi-dimensional parameter space representation is displayed of possible combinations of the plurality of edge detection parameters. At a block 530, a parameter combination indicator located within the multidimensional parameter space representation is displayed which indicates a combination of at least two of the plurality of edge detection parameters based on its location. At a block 540, at least one edge feature representation window is displayed that represents edge features located in the region of interest of the edge location video tool. The at least one edge feature representation window responds to the configuration of the parameter combination indicator as it is modified by a user such that edge features detectable by the combination of edge detection parameters indicated by a current configuration of the parameter combination indicator are automatically updated in the at least one edge feature representation window.

Figure 6:
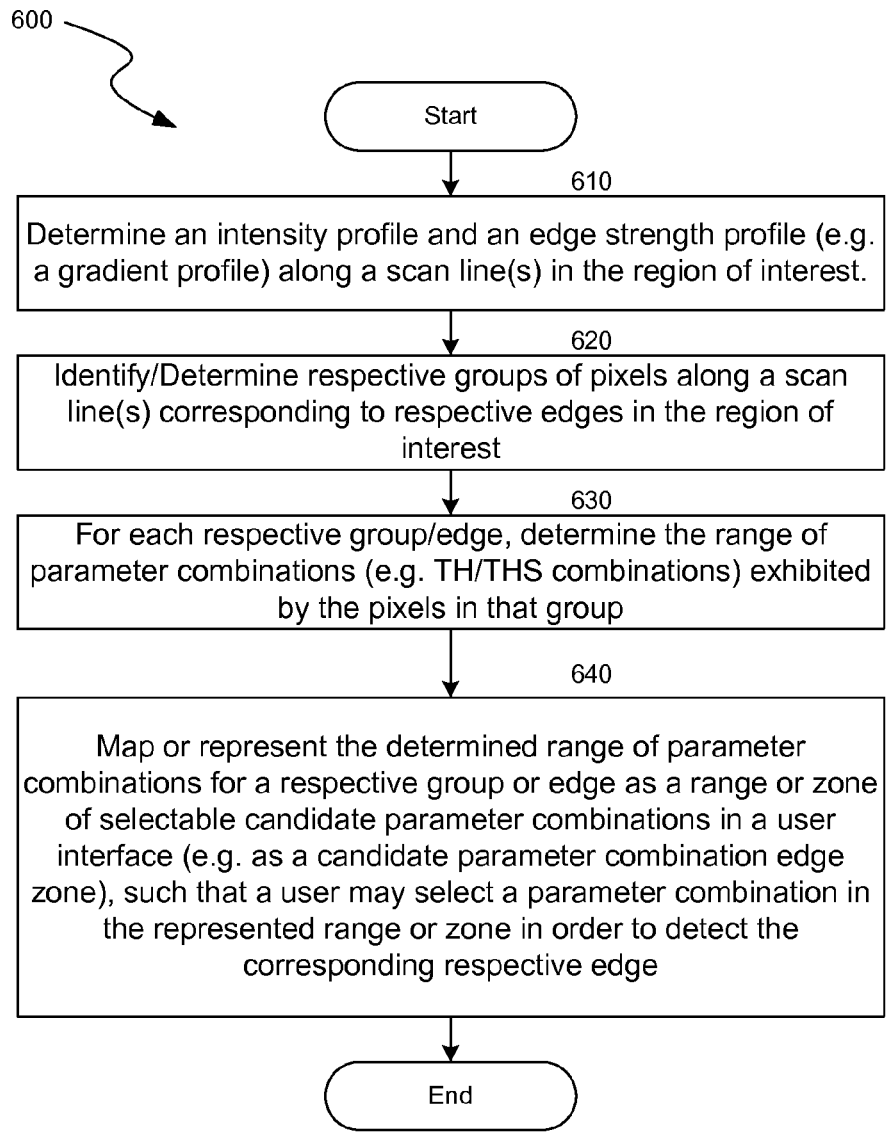
FIG. 6 is a flow diagram of a method for displaying a multi-dimensional parameter space representation with edge zones.

FIG. 6 is a flow diagram illustrating one exemplary embodiment of a routine 600 for determining candidate parameter combination edge zones such as those shown in FIGS. 3 and 4. As will be described in more detail below, in this particular embodiment, the method generally comprises operations that identify a group of scanline pixels that correspond to a particular edge, determine the range of TH and THS edge detection parameter values/combinations that are exhibited by that group of pixels, and represent that range of TH and THS values/combinations as a corresponding range or zone of selectable candidate parameter combinations in a user interface, such that a user may select a parameter combination in the represented range or zone in order to detect the edge corresponding to that zone. One embodiment of these steps will be described below more specifically with respect to FIG. 6.

As shown in FIG. 6, at a block 610, an intensity profile and an edge strength profile (e.g. a gradient profile) are determined along a scan line(s) in the region of interest. At a block 620, respective groups of pixels along a scan line(s) corresponding to respective edges in the region of interest are determined (e.g. by identifying a group of adjacent pixels that exhibit a significant intensity increase (decrease), for a rising (falling) edge). At a block 630, for each respective group, the range of parameter combinations (e.g. TH/THS combinations) exhibited by the pixels in that group are determined.

At a block 640, the determined range of parameter combinations for a respective group or edge are mapped or represented as candidate parameter combinations represented as a range or zone of selectable candidate parameter combinations in a user interface (e.g. as a candidate parameter combination edge zone), such that a user may select a parameter combination in the represented range or zone in order to detect the corresponding respective edge.

Figure 7:
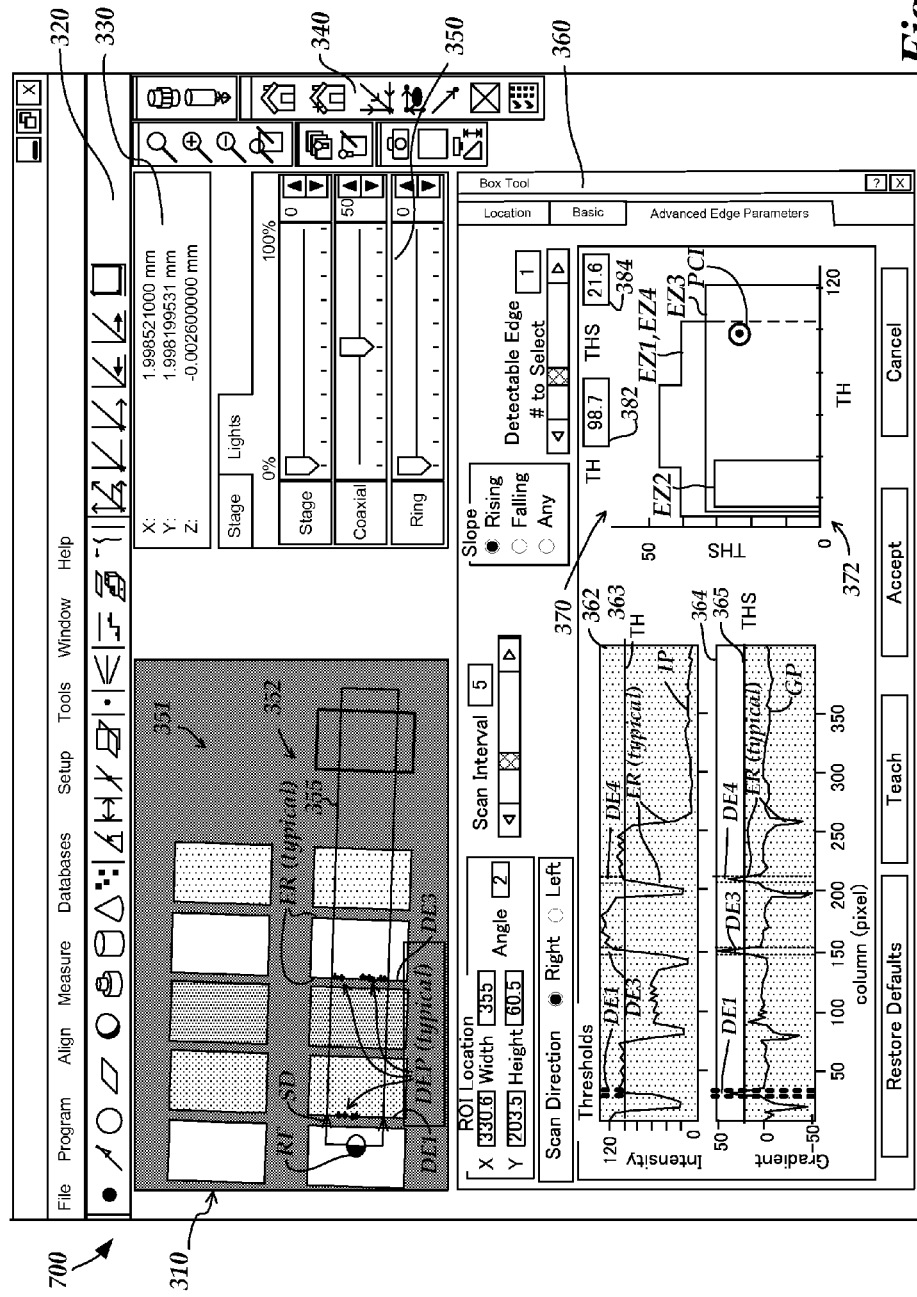
FIGS. 7 and 8 are diagrams illustrating various features of a second embodiment of a user interface display including a multi-dimensional parameter space representation with edge zones and a video window including edge feature representations and superimposed detected edge points.
Figure 8:
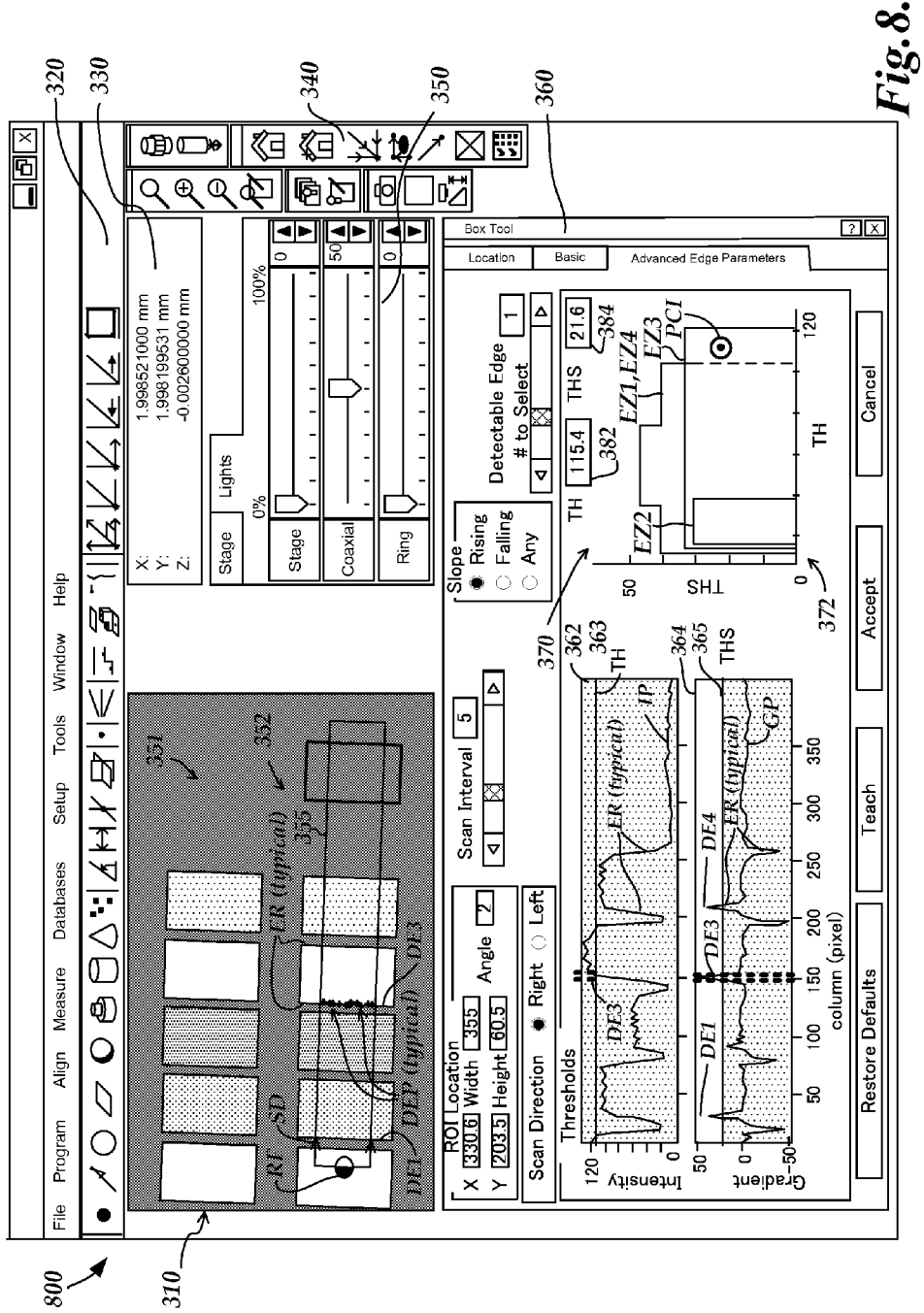

FIGS. 7 and 8 are diagrams illustrating various features of a second embodiment of a user interface display 700 including a multi-dimensional parameter space representation and a field of view window 310 including edge feature representations ER and superimposed detected edge points DEP. Otherwise, the user interface display 700 may be similar to the user interface display 300 shown in FIGS. 3 and 4, and similarly numbered elements may be understood by analogy unless otherwise indicated.

As previously indicated, in the field of view window 310 edge features are understood to be represented by their image, as indicated by the edge feature representations ER, for example. The multi-dimensional parameter space representation 370 includes a two dimensional graph 372 showing potential combinations of edge detection parameters TH and THS, with a current combination of the parameters indicated by the location of a parameter combination indicator PCI. Parameter combination edge zones EZ1, EZ2, EZ3 and EZ4 are indicated within the multi-dimensional parameter space representation 370. In the embodiment shown in FIGS. 7 and 8, the scan line intensity window 362 and scan line gradient window 364 illustrate graphs of a scanline intensity profile IP and a scanline intensity gradient profile GP at pixel locations along the scanline direction for a representative scanline (e.g. a central or average scanline, or the like) across the region of interest. The edge features detectable by the current combination of the edge detection parameters TH and THS (the detectable edges DE) are displayed and automatically updated in the windows 362 and 364, as previously described. In the field of view window 310 detected edge points DEP that satisfy the current combination of parameters are indicated, as described in greater detail below.

In the case shown in FIG. 7, in comparison to FIG. 3, a user has repositioned the parameter combination indicator PCI to be within the parameter combination edge zones EZ1, EZ3 and EZ4 and such that the edge detection parameter TH has a value 98.7. The three edge representations that satisfy the current combination of parameters are highlighted or indicated as detectable edges in the windows 362 and 364 by the unshaded areas marked as DE1, DE3 and DE4.

An important feature added in user interface display 700 in comparison to the user interface display 300 is that in the field of view window 310 detected edge points DEP that satisfy the current combination of parameters are indicated. This provides more information than the representations in the user interface display 300. For example, it may be seen in the scan line intensity window 362 that the parameter TH is set such that the detectable edge DE1 of the representative scan line that is illustrated in the window 362 barely exceeds the parameter TH. However, importantly, the detected edge points DEP in the field of view window 310 indicate that along only a few of the scan lines does the detectable edge DE 1 exceeds the parameter TH. Thus, the detected edge points DEP in the field of view window 310 also indicate that along some of the scan lines the first rising edge that exceeds the parameter TH correspond to the detectable edge DE3. Such visual indications assist users with understanding how changes in the edge detection parameters TH and THS, separately and in combination, affect the determination of edges and provide a real time indication of how the algorithm is working. In the case shown in FIG. 7, the detected edge points DEP clearly and immediately illustrate that the current parameters do not distinguish reliably between the edges DE1 and DE3.

In contrast, as shown in FIG. 8, the indicator PCI in the graph 372 has been moved to a new location (e.g. by dragging in the user interface) to only be within the parameter combination edge zone EZ3. In the embodiment of FIGS. 7 and 8, the windows 362 and 364 and 310 are all synchronized with the multi-dimensional parameter space representation 370, such that an adjustment in the position of the indicator PCI results in a corresponding adjustment in the level of the TH line 363 and the THS line 365, as well as the detected edge points DEP. As a result of the particular new levels defined for the parameters TH and THS, only the edge indicated by the reference number DE3 in the windows 362 and 364, is now indicated as a detectable edge. Perhaps more importantly, it may be seen in the window 310 that the detected edge points DEP are also now all located at the corresponding detectable edge DE3, conveying the information that the current set of parameters distinguish the edge DE3 from all other edges along all scan lines, not just along the representative scan line in the windows 362 and 364. In fact, a user may perhaps drag the PCI and set the parameters more reliably by observing the corresponding detected edge points DEP than by observing the windows 362 and 364, in some embodiments. Thus, in some embodiments where detected edge points DEP are illustrated in the field of view window 310, the windows 362 and 364 may be optional, or omitted, and/or hidden unless selected for display by the user.

Figure 9:
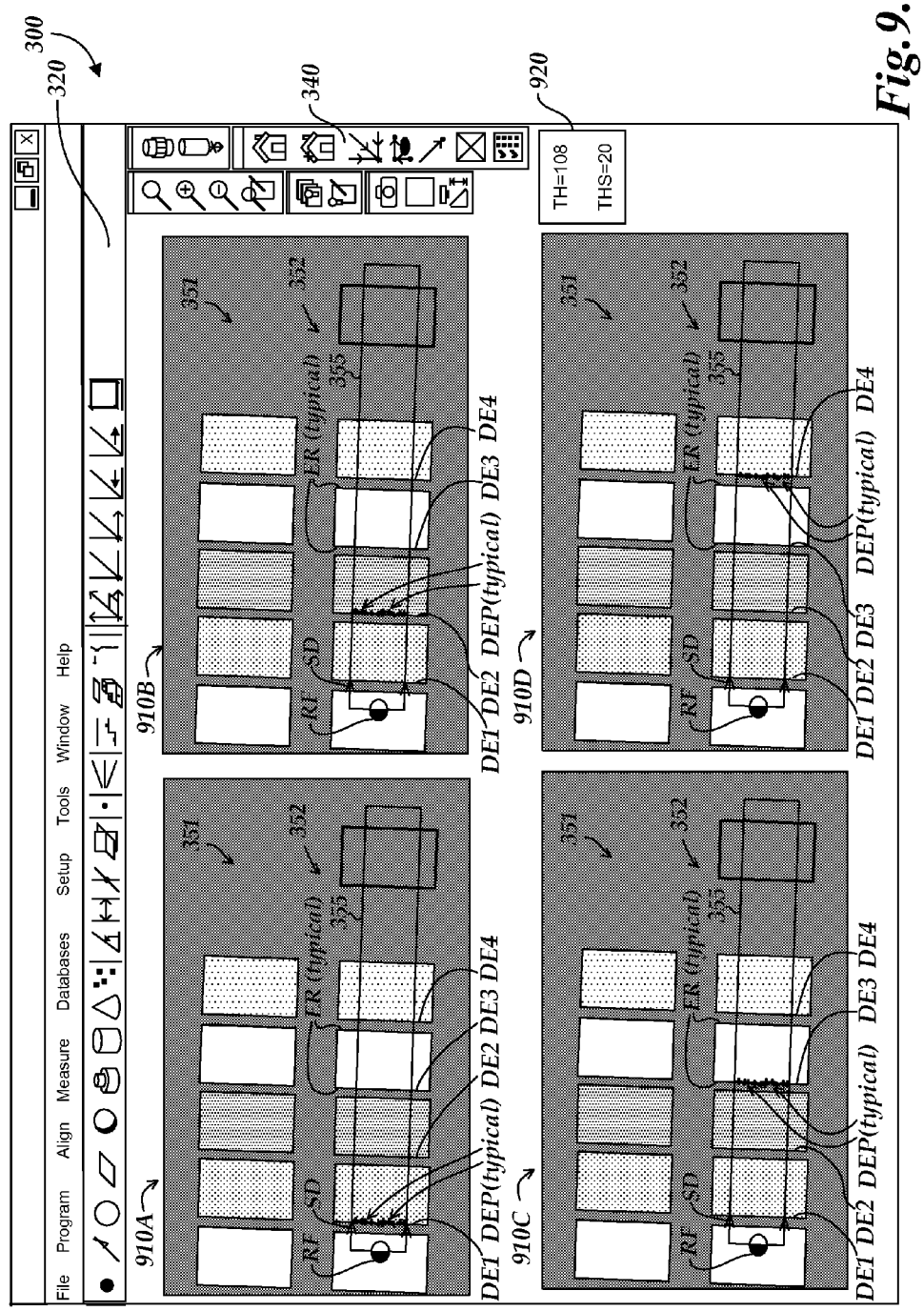

FIG. 9 is a diagram illustrating various features of a third embodiment of a user interface display 900 including different edge feature representations provided in a series of field of view windows 910A-910D that a user can select from. The field of view windows 910A-910D are similar to the field of view window 310 described above with respect to FIGS. 3, 4, 7 and 8, and similarly numbered elements may be understood by analogy unless otherwise indicated.

The field of view windows 910A-910D primarily differ from one another in accordance with the locations of detected edge points DEP. As shown in the window 910A, the detected edge points DEP are located on a first detectable edge DE1. In contrast, in the window 910B, the detected edge points DEP are located on a second detectable edge DE2. Similarly, in the window 910C, the detected edge points DEP are located on a third detectable edge DE3, and in the window 910D, the detected edge points DEP are located on a fourth detectable edge DE4. A parameter indicator box 920 is provided which indicates parameter values TH and THS (a parameter combination) corresponding to the current selected field of view window. In one embodiment, the candidate parameter combination indicated in the indicator box 920, which may result in the particular displayed detected edge points DEP, may be an estimated best combination for detecting the corresponding edge (e.g., in one embodiment, a median or average parameter combination from a parameter combination range exhibited by the edge points of the corresponding edge). As described above with respect to the example of FIGS. 7 and 8, different parameter combinations of the edge detection parameters TH and THS may result in different detected edge points DEP. As will be described in more detail below, each of the field of view windows 910A-910D represents a different candidate parameter combination of the edge detection parameters TH and THS (and/or other edge parameters, such as an edge number parameter, in some embodiments), which results in the different locations of the detected edge points DEP.

In one embodiment, in order to produce the field of view windows 910A-910D, the system automatically scans the search space of the edge detection parameters and generates images (e.g. field of view windows) showing meaningful variations of the edge detection results that occur in response to candidate edge detection parameter combinations. As will be described in more detail below with respect to FIGS. 10 and 11, this process may be performed utilizing various techniques (e.g. an exhaustive parameter space search, a feature-guided search, etc.). In an alternative embodiment, a single field of view window may be provided, wherein different detectable edges are indicated in the single field of view (e.g. by color coding of detected edge points at each edge, or superimposed numbering, or the like). A user is then able to simply choose the desirable candidate parameter combination (e.g. by clicking on a field of view window or a selected edge feature) in order to set the corresponding edge detection parameters for the video tool. It will be appreciated that by displaying the results of various possible candidate edge detection combinations, a user is also effectively shown what the system is capable of detecting in a given region of interest, which allows a user to make informed choices regarding the edges to be detected.

It will be appreciated that the embodiment illustrated by FIG. 9 simplifies the edge detection threshold setting process, and may reduce user frustration. In other words, in previous systems where a user was required to manually set individual edge detection parameters, the process could often be confusing and time consuming. Even with the improved methods described above with respect to FIGS. 3-8, in particular in an implementation where the parameter combination edge zones are not indicated, the adjustments to the edge detection parameters may still be somewhat confusing, in that the mechanism of how the thresholds affect the edge location is not intuitive and is often understood by only the most advanced users.

In one embodiment, after a user chooses the desired candidate parameter combination (e.g. the user clicks on one of the field of view windows 910A-910D), the user may then further fine-tune the parameter settings (e.g. within a wider range of candidate parameter combinations exhibited by the corresponding edge points) utilizing the user interface and techniques described above with respect to FIGS. 3-8.) In certain implementations, allowing a user to fine-tune the settings may be beneficial to certain edge detection techniques, in particular those that do not utilize feature detection (e.g. line, arc, etc.) in the edge detection algorithm. For the fine-tuning, in certain implementations the user may drag the edge in the image (or the edge selector as illustrated in FIGS. 3 and 4) directly, from which the algorithm will automatically relearn the edge detection parameters. For certain edges that are not detectable when they are shadowed by a previous edge along a scan line direction, a user may be provided with directions to move or alter a GUI element to exclude the shadowing edge, or a suggestion to utilize a different tool, such as an edge selection tool.

Figure 10:
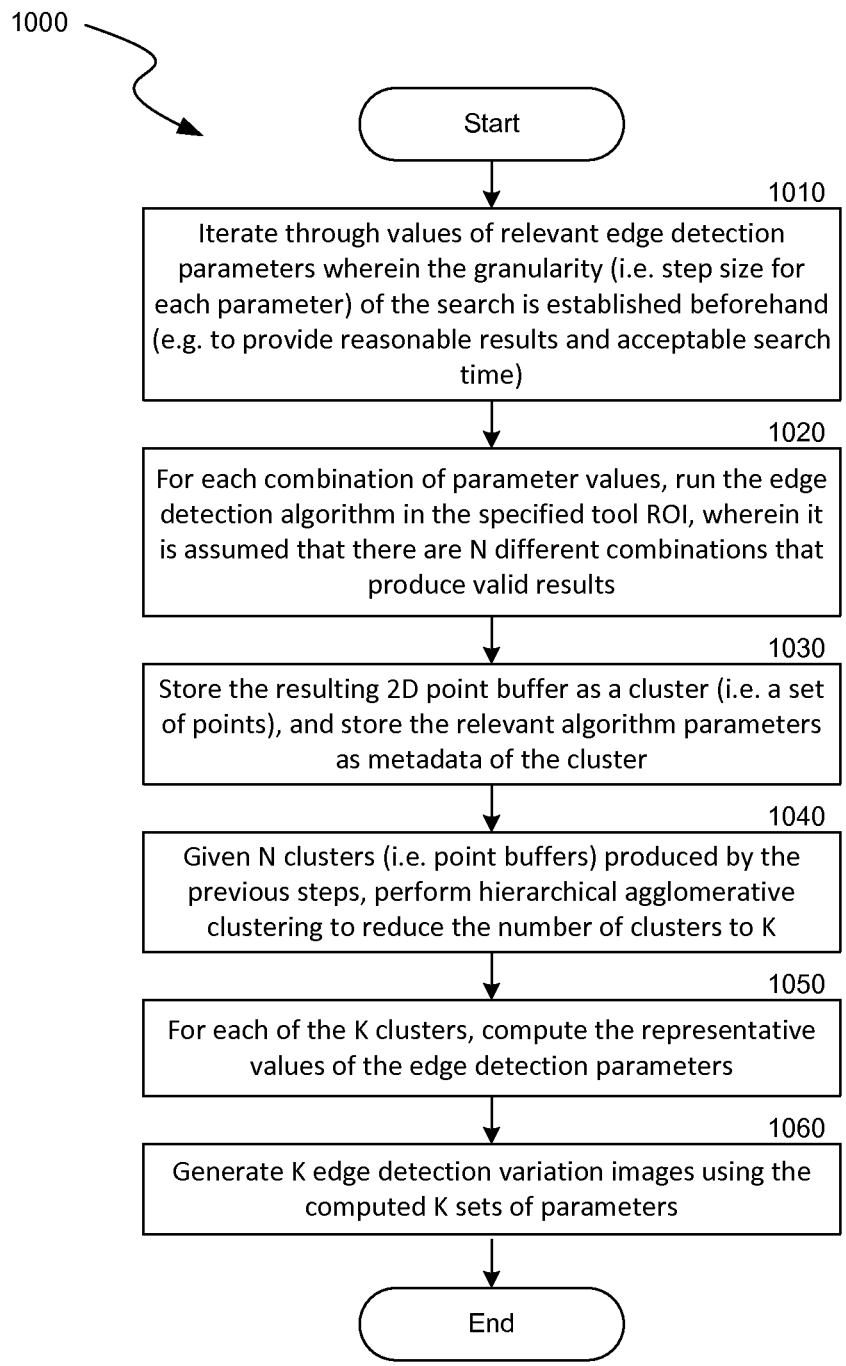

FIG. 10 is a flow diagram of a method 1000 utilizing an exhaustive search for determining and displaying different edge feature representations that a user can select from, such as those illustrated in FIG. 9. As will be described in more detail below, in one implementation, the method may generally be directed toward generating a set of edge detection results in which each result (i.e. variation) is "different enough" or "significantly different" from the remaining results so as to provide a user with meaningful options to select from, and may primarily be utilized during a learn mode. As shown in FIG. 10, at a block 1010, values of relevant edge detection parameters are iterated through, wherein the granularity (i.e. step size for each parameter) of the search is established beforehand (e.g. to provide reasonable results and an acceptable search time.)

At a block 1020, for each combination of parameter values, the edge detection algorithm is run in the specified tool region of interest, wherein it is assumed that there are N different combinations that produce valid results. In one implementation, combinations that produce very small point buffers (e.g. relatively few points) may be discarded. A threshold may be utilized for the minimum number of points that a point buffer is expected to deliver. At a block 1030, the resulting 2D point buffer is stored as a cluster (i.e. a set of points), and the relevant algorithm parameters are stored as metadata of the cluster. In one implementation, the blocks 1010-1030 may be repeated for all N combinations of parameter values.

At a block 1040, given N clusters (point buffers) produced by the previous steps, hierarchical agglomerative clustering is performed to reduce the number of clusters to a number K. In one implementation, the hierarchical agglomerative clustering algorithm may operate in the following manner. The process begins with N clusters, each consisting of one 2D point buffer returned by the edge detection algorithm. Then, the two most similar clusters A and B are found and are merged into one cluster if they are similar enough (this process is repeated up to N−1 times, if needed.) If no two clusters are similar enough, the clustering process ends. If a tie occurs (i.e. two pairs of clusters have equal similarity), the first pair that is found is merged. In one implementation, the similarity of two clusters may be measured using a distance measure, as will be described in more detail below. In one implementation, the "similar enough" requirement is determined according to whether the distance between the two clusters is smaller than a predefined distance threshold.

Various distance measures may be utilized for agglomerative clustering. In one implementation, a Hausdorff distance (i.e. a maximum distance of a set to the nearest point in the other set) is utilized (e.g. see http://cgm.cs.mcgill.ca/~godfried/teaching/cg-projects/98/normand/main.html.) In another implementation, a modified Hausdorff-like distance DH may be more suitable to reduce sensitivity to outliers in point buffers, wherein: D(A, B)=fraction of points in cluster A that are "not close enough" to the nearest point in cluster B ("not close enough" meaning the Euclidean distance between points is larger than a predefined threshold); D(B, A)=fraction of points in cluster B that are "not close enough" to the nearest point in cluster A; and DH=max{D(A,B), D(B,A)}. Other cluster distance measures may also be utilized (e.g. average-linkage or minimum-variance such as Ward's method, etc.)

Returning to FIG. 10, at a block 1050, for each of the K clusters, the representative values of the edge detection parameters are computed. In one implementation, since each cluster A of the K final clusters is an aggregate of one or more of the original clusters (i.e. point buffers), the representative values for each parameter can be computed (e.g. as a median or average of the values of that parameter for all the original clusters belonging to cluster A.) At a block 1060, K edge detection variation images are generated using the computed K sets of parameters.

It will be appreciated that in certain implementations the exhaustive search technique described above with respect to FIG. 10 may take a relatively longer time to perform than certain other techniques (e.g. due to the edge detection needing to be done N times, once for each setting). However, the overall timing may still be relatively short (i.e. the basic edge detection processes can be performed relatively quickly, for which the entire process may in some implementations take less than a few seconds.) Such timing may be acceptable for certain applications (e.g. when the process is being utilized as part of a learn-mode procedure where timing considerations are not as critical, etc.) In certain implementations, a matrix of inter-point distances for all points detected in N combinations may be precomputed in order to avoid repeated calculations during the clustering process, which allows the process to be performed more quickly.

Figure 11:
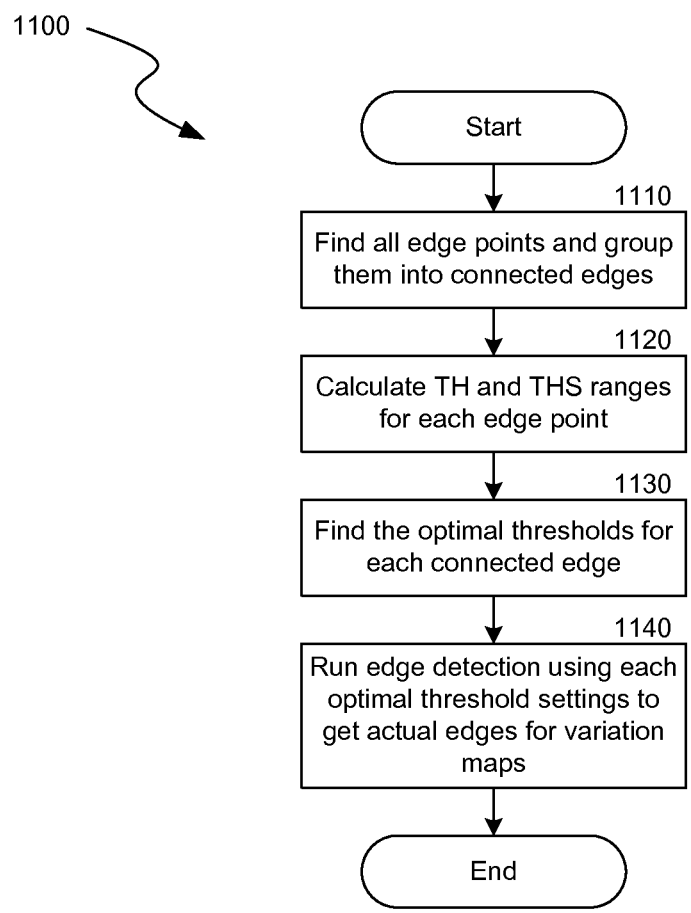

FIG. 11 is a flow diagram of a method 1100 utilizing connected edges for determining and displaying different edge feature representations that a user can select from, such as those illustrated in FIG. 9. In other words, as an alternative to utilizing exhaustive searching as described above with respect to FIG. 10, in one implementation the edges may instead be grouped into edge features, and then appropriate thresholds may be found for each edge feature. In certain implementations, this method utilizing connected edges may be performed more rapidly than a method utilizing exhaustive searching.

As shown in FIG. 11, at a block 1110, all of the edge points are found and are grouped into connected edges. In various implementations, this process may utilize techniques such as: Canny edge detection followed by edge linking; segmentation followed by edge tracing; any combination of segmentation and edge detection; 1D projection to identify all possible lines and arcs, etc. At a block 1120, the TH and THS ranges are calculated for each edge point. As described above, in general for certain standard edge detection processes, each edge point may only be found when the TH and THS are within certain ranges. It will be appreciated that in certain implementations some edge points may have null ranges of TH and THS (e.g. due to an "early-out" process of the particular edge detection algorithm that is utilized, etc.)

At a block 1130, for each connected edge, the optimal thresholds are found. In certain implementations, the optimal thresholds may be determined according to criteria such as: maximum number of inliers; minimum number of outliers; robustness to image noise, etc. In one embodiment, if the edge points along a connected edge have significantly different ranges of thresholds, a technique may be utilized to break the edge down into segments of similar edges (e.g. by divisive clustering, etc). At a block 1140, edge detection is run using each optimal threshold settings to produce actual edges for the variation maps. In one embodiment, when the number of variation maps is large, a number of the most significant maps (e.g. 10) may be presented, and a user may then select the map that is closest to the desired values and then be allowed to further manually adjust the thresholds.

Figure 12:
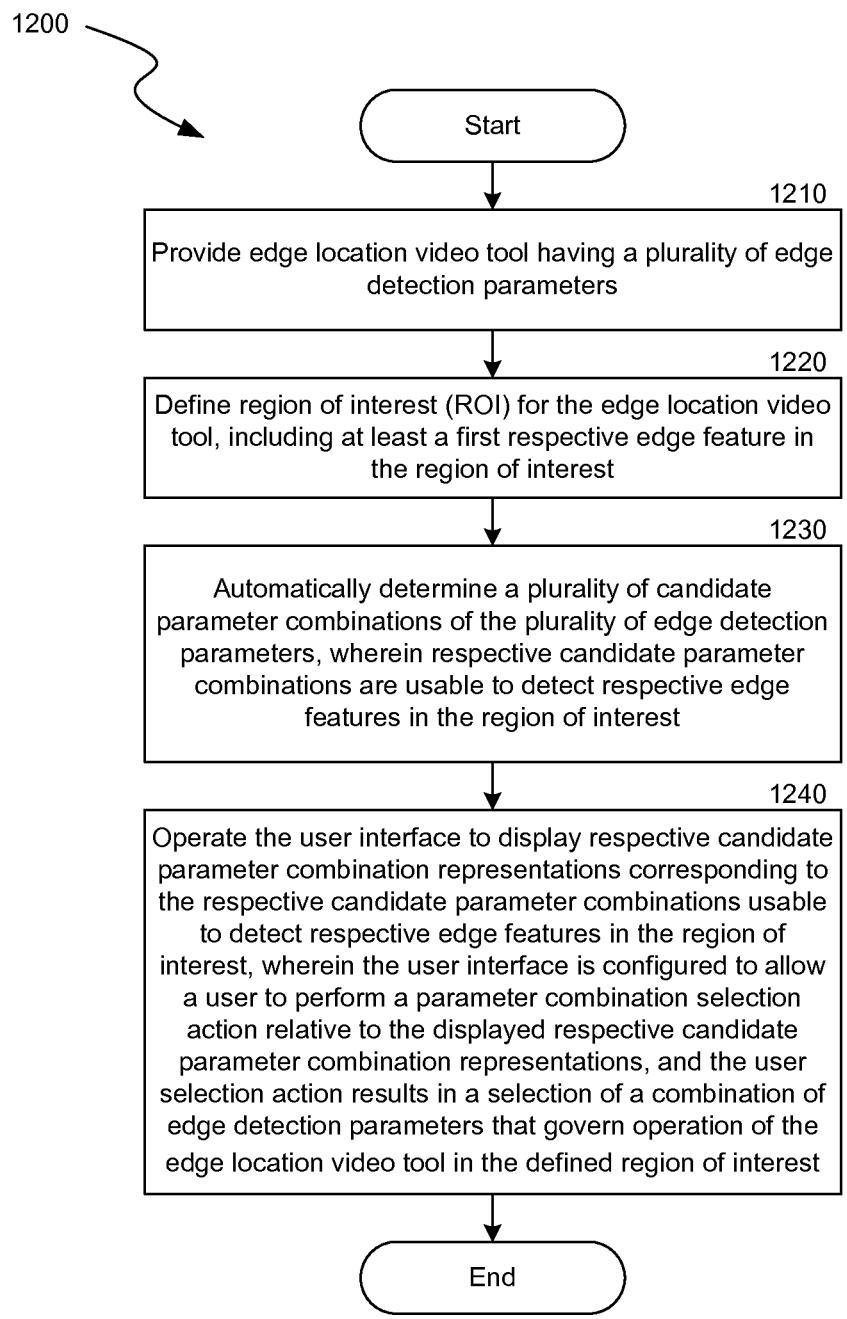
FIG. 12 is a flow diagram of a method for automatically determining a plurality of candidate parameter combinations of a plurality of edge detection parameters.

FIG. 12 is a flow diagram of a method 1200 for automatically determining a plurality of candidate parameter combinations. At a block 1210, an edge location video tool having a plurality of edge detection parameters is provided. At a block 1220, a region of interest (ROI) for the edge location video tool is defined, including at least a first respective edge feature in the region of interest. At a block 1230, a plurality of candidate parameter combinations of the plurality of edge detection parameters are automatically determined, wherein respective candidate parameter combinations are usable to detect respective edge features in the region of interest. At a block 1240, the user interface is operated to display respective candidate parameter combination representations corresponding to the respective candidate parameter combinations usable to detect respective edge features in the region of interest, and the user interface is configured to allow a user to perform a parameter combination selection action relative to the displayed respective candidate parameter combination representations. The user selection action results in a selection of a combination of edge detection parameters that govern operation of the edge location video tool in the defined region of interest.

From the foregoing, it will be appreciated that specific embodiments of the invention have been described herein for purposes of illustration, but that various modifications may be made without deviating from the scope of the invention. For example, a multidimensional parameter space representation may include adding a third dimension to a two dimensional grid to form a volume (e.g. represented isometrically, and/or rotatably, or the like), and locating a parameter combination indicator in the volume. Or, a two dimensional grid may be augmented with a nearby linear parameter space representation for a third parameter, or the like. As another example, it will be appreciated that image processing operations (e.g. filtering operations) may be applied to a region of interest and/or edges therein to improve or reveal a property of an edge (or edges) which makes edge detection or discrimination possible, or more reliable. For example, texture edges, color edges or the like, may represent in a filtered image, or pseudo-image, or the like, and the systems and methods disclosed herein may be applied to such images to supplement or replace the various operations outlined herein. Accordingly, the invention is not limited except as by the appended claims.

We claim:

1. A method for defining edge detection parameters in a machine vision inspection system user interface, the method comprising:
    providing an edge location video tool having a plurality of edge detection parameters;
    defining a region of interest (ROI) for the edge location video tool, including at least a first respective edge feature in the region of interest;
    automatically determining a plurality of candidate parameter combinations of the plurality of edge detection parameters, wherein respective candidate parameter combinations are usable to detect respective edge features in the region of interest; and
    operating the user interface to simultaneously display a plurality of respective candidate parameter combination representations corresponding to the respective candidate parameter combinations usable to detect respective edge features in the region of interest, wherein the user interface is configured to allow a user to perform a parameter combination selection action relative to the simultaneously displayed plurality of respective candidate parameter combination representations, the user selection action resulting in a selection of a combination of edge detection parameters that govern operation of the edge location video tool in the defined region of interest.

2. The method of claim 1, wherein:
    the user interface comprises a multi-dimensional parameter space representation of possible combinations of the plurality of edge detection parameters;
    the step of automatically determining a plurality of candidate parameter combinations comprises automatically determining a first set of respective candidate parameter combinations usable to detect the first respective edge feature; and
    the step of operating the user interface to simultaneously display a plurality of respective candidate parameter combination representations comprises displaying a representation of a first set of respective candidate parameter combinations as a first zone in the multi-dimensional parameter space representation.

3. The method of claim 2, wherein:
    the user interface is configured to allow a user to perform a parameter combination selection action relative to the first zone, comprising moving a parameter combination indicator to a location within the first zone and operating the parameter combination indicator to select the parameter combination corresponding to that location.

4. The method of claim 3, wherein:
    the region of interest (ROI) includes at least a second respective edge feature in the region of interest;
    the step of automatically determining a plurality of candidate parameter combinations comprises automatically determining a second set of respective candidate parameter combinations usable to detect the second respective edge feature; and
    the step of operating the user interface to simultaneously display a plurality of respective candidate parameter combination representations comprises displaying a representation of the second set of respective candidate parameter combinations as a second zone in the multi-dimensional parameter space representation.

5. The method of claim 4, wherein the user interface further comprises at least one edge feature representation window that includes an image of the field of view of the machine vision inspection system and a representation of the edge features detectable by the combination of parameters indicated by a current configuration of the parameter combination indicator superimposed on the image of the field of view.

6. The method of claim 5, wherein the representation of the edge features detectable by the combination of parameters indicated by the current configuration of the parameter combination indicator comprises a plurality of detectable edge points, corresponding to a plurality of scan lines across the ROI, superimposed on the image of the field of view.

7. The method of claim 6, wherein the at least one edge feature representation window and the multi-dimensional parameter space representation are synchronized such that an adjustment or selection in the at least one edge feature representation window results in a corresponding indication in the multi-dimensional parameter space representation.

8. The method of claim 1, wherein:
    the region of interest (ROI) includes at least a second respective edge feature in the region of interest;
    the step of automatically determining a plurality of candidate parameter combinations comprises determining at least a first respective candidate parameter combination usable to detect the first respective edge feature, and determining at least a second respective candidate parameter combination usable to detect the second respective edge feature; and
    the step of operating the user interface to simultaneously display a plurality of respective candidate parameter combination representations comprises:
        displaying a representation of the first respective edge feature as a first respective candidate parameter combination representation that corresponds to the first respective candidate parameter combination; and
        displaying a representation of the second respective edge feature as a second respective candidate parameter combination representation that corresponds to the second respective candidate parameter combination.

9. The method of claim 8, wherein:
    the user interface is configured to allow a user to perform a parameter combination selection action relative to the displayed representations of the first and second respective edge features, comprising moving a cursor to a location proximate to the representation of a desired one of the first and second respective edge features and operating the cursor to select the parameter combination corresponding to that edge feature.

10. The method of claim 8, wherein:
    the representation of the first and second respective edge features comprises a first indicator superimposed on an image of the first respective edge feature indicating that the first respective candidate parameter combination has been determined, and a second indicator superimposed on an image of the second respective edge feature indicating that the second respective candidate parameter combination has been determined.

11. The method of claim 10, wherein the first and second indicators comprise detected edge points along the first and second edge features, respectively.

12. The method of claim 8, wherein:
the representation of the first respective edge feature comprises a first edge window including the first respective edge feature indicating that the first respective candidate parameter combination has been determined, and the representation of the second respective edge feature comprises a second edge window including the second respective edge feature indicating that the second respective candidate parameter combination has been determined; and
the user interface is configured to allow a user to perform a parameter combination selection action relative to the displayed representations of the first and second respective edge features, comprising moving a cursor to a location in a desired one of the first and second edge windows and operating the cursor to select the parameter combination corresponding to that edge feature.

13. The method of claim 8, wherein:
the user interface further comprises a multi-dimensional parameter space representation of possible combinations of the plurality of edge detection parameters; and
the user interface is configured to allow a user to perform a parameter combination selection action relative to the displayed representations of the first and second respective edge features, comprising moving a cursor to a location proximate to the representation of a desired one of the first and second respective edge features and operating the cursor to select either the first or second respective edge feature, in response to which the user interface is further configured to display one of:
a representation of a first set of respective candidate parameter combinations as a first zone in the multi-dimensional parameter space representation if the first respective edge feature is selected, wherein the first set of respective parameter combinations comprises the first respective candidate parameter combination usable to detect the first respective edge feature in addition to other candidate parameter combinations usable to detect the first respective edge feature; or
a representation of a second set of respective candidate parameter combinations as a second zone in the multi-dimensional parameter space representation if the second respective edge feature is selected, wherein the second set of respective parameter combinations comprises the second respective candidate parameter combination usable to detect the second respective edge feature in addition to other candidate parameter combinations usable to detect the second respective edge feature.

14. A system for defining edge detection parameters in a machine vision inspection system user interface, comprising:
a memory for storing programmed instructions;
a processor configured to execute the programmed instructions to perform operations including:
providing an edge location video tool having a plurality of edge detection parameters;
defining a region of interest (ROI) for the edge location video tool, including at least a first respective edge feature in the region of interest;
automatically determining a plurality of candidate parameter combinations of the plurality of edge detection parameters, wherein respective candidate parameter combinations are usable to detect respective edge features in the region of interest; and
operating the user interface to simultaneously display a plurality of respective candidate parameter combination representations corresponding to the respective candidate parameter combinations usable to detect respective edge features in the region of interest, wherein the user interface is configured to allow a user to perform a parameter combination selection action relative to the simultaneously displayed a plurality of respective candidate parameter combination representations, the user selection action resulting in a selection of a combination of edge detection parameters that govern operation of the edge location video tool in the defined region of interest.

15. The system of claim 14, wherein:
the user interface comprises a multi-dimensional parameter space representation of possible combinations of the plurality of edge detection parameters;
the step of automatically determining a plurality of candidate parameter combinations comprises automatically determining a first set of respective candidate parameter combinations usable to detect the first respective edge feature; and
the step of operating the user interface to simultaneously display a plurality of respective candidate parameter combination representations comprises displaying a representation of a first set of respective candidate parameter combinations as a first zone in the multi-dimensional parameter space representation.

16. The system of claim 14, wherein:
the region of interest (ROI) includes at least a second respective edge feature in the region of interest;
the step of automatically determining a plurality of candidate parameter combinations comprises determining at least a first respective candidate parameter combination usable to detect the first respective edge feature, and determining at least a second respective candidate parameter combination usable to detect the second respective edge feature; and
the step of operating the user interface to simultaneously display a plurality of respective candidate parameter combination representations comprises:
displaying a representation of the first respective edge feature as a first respective candidate parameter combination representation that corresponds to the first respective candidate parameter combination; and
displaying a representation of the second respective edge feature as a second respective candidate parameter combination representation that corresponds to the second respective candidate parameter combination.

17. The system of claim 16, wherein:
the user interface is configured to allow a user to perform a parameter combination selection action relative to the displayed representations of the first and second respective edge features, comprising moving a cursor to a location proximate to the representation of a desired one of the first and second respective edge features and operating the cursor to select the parameter combination corresponding to that edge feature.

18. A computer readable non-transitory storage medium with instructions stored thereon that are executable by a processor to perform operations of:

providing an edge location video tool having a plurality of edge detection parameters;

defining a region of interest (ROI) for the edge location video tool, including at least a first respective edge feature in the region of interest;

automatically determining a plurality of candidate parameter combinations of the plurality of edge detection parameters, wherein respective candidate parameter combinations are usable to detect respective edge features in the region of interest; and operating the user interface to simultaneously display a plurality of respective candidate parameter combination representations corresponding to the respective candidate parameter combinations usable to detect respective edge features in the region of interest, wherein the user interface is configured to allow a user to perform a parameter combination selection action relative to the simultaneously displayed plurality of respective candidate parameter combination representations, the user selection action resulting in a selection of a combination of edge detection parameters that govern operation of the edge location video tool in the defined region of interest.

19. The computer readable non-transitory storage medium of claim 18, wherein:

the user interface comprises a multi-dimensional parameter space representation of possible combinations of the plurality of edge detection parameters;

the step of automatically determining a plurality of candidate parameter combinations comprises automatically determining a first set of respective candidate parameter combinations usable to detect the first respective edge feature; and the step of operating the user interface to simultaneously display a plurality of respective candidate parameter combination representations comprises displaying a representation of a first set of respective candidate parameter combinations as a first zone in the multi-dimensional parameter space representation.

20. The computer readable non-transitory storage medium of claim 18, wherein:

the region of interest (ROI) includes at least a second respective edge feature in the region of interest;

the step of automatically determining a plurality of candidate parameter combinations comprises determining at least a first respective candidate parameter combination usable to detect the first respective edge feature, and determining at least a second respective candidate parameter combination usable to detect the second respective edge feature; and the step of operating the user interface to simultaneously display a plurality of respective candidate parameter combination representations comprises:

displaying a representation of the first respective edge feature as a first respective candidate parameter combination representation that corresponds to the first respective candidate parameter combination; and displaying a representation of the second respective edge feature as a second respective candidate parameter combination representation that corresponds to the second respective candidate parameter combination.

* * * * *